US012797130B2

(12) United States Patent
Mercer et al.

(10) Patent No.: US 12,797,130 B2
(45) Date of Patent: Nov. 17, 2026

(54) SOFT TISSUE BALANCING IN KNEE REPLACEMENT

(71) Applicant: DEPUY IRELAND UNLIMITED COMPANY, Ringaskiddy (IE)

(72) Inventors: Alasdair Mercer, Leeds (GB); David Wolfson, Batley (GB); Michael J. Rock, Leeds (GB)

(73) Assignee: DEPUY IRELAND UNLIMITED COMPANY, LOUGHBEG INDUSTRIAL ESTATE, Ringaskiddy (IE)

( * ) Notice: Subject to any disclaimer, the term of this patent is extended or adjusted under 35 U.S.C. 154(b) by 1116 days.

(21) Appl. No.: 17/904,438

(22) PCT Filed: Feb. 23, 2021

(86) PCT No.: PCT/EP2021/054474
§ 371 (c)(1),
(2) Date: Aug. 17, 2022

(87) PCT Pub. No.: WO2021/170591
PCT Pub. Date: Sep. 2, 2021

(65) Prior Publication Data

US 2023/0066132 A1 Mar. 2, 2023

(30) Foreign Application Priority Data

Feb. 28, 2020 (GB) ...................................... 2002918

(51) Int. Cl.
*A61B 34/10* (2016.01)
*A61B 34/20* (2016.01)
*A61B 34/30* (2016.01)

(52) U.S. Cl.
CPC .............. *A61B 34/10* (2016.02); *A61B 34/30* (2016.02); *A61B 2034/2055* (2016.02)

(58) Field of Classification Search
CPC .. A61B 34/10; A61B 34/30; A61B 2034/2055
(Continued)

(56) References Cited

U.S. PATENT DOCUMENTS 6,022,377 A 2/2000 Nuelle
7,156,853 B2 1/2007 Muratsu
(Continued)

FOREIGN PATENT DOCUMENTS

JP 20102404034 A 10/2010
WO 2005023120 A1 3/2005
(Continued)

OTHER PUBLICATIONS

Japanese Notice of Reasons for Refusal for Patent Application 2022-551666, Dated Nov. 27, 2024, 10 Pages.
(Continued)

*Primary Examiner* — Chanel J Yoon

(57) ABSTRACT

A surgical planning method carried out by a data processing apparatus that comprises determining a lateral force-distance characteristic for each of a plurality of knee flexion angles, determining a medial force-distance characteristic for each of the plurality of knee flexion angles, using a lateral force-distance characteristic to determine a lateral knee gap distance corresponding to a target force for at least one of the plurality of knee flexion angles, and using a medial force-displacement characteristic to determine a medial knee gap distance corresponding to a target force for at least one of the plurality of knee flexion angles. The method also comprises outputting the lateral knee gap distance corresponding to the target force and the medial knee gap distance corresponding to the target force as a function of knee flexion angle.

10 Claims, 17 Drawing Sheets

(58) Field of Classification Search
USPC .......................................................... 600/587
See application file for complete search history.

(56) References Cited

U.S. PATENT DOCUMENTS

| | | | |
|---|---|---|---|
| 7,575,602 | B2 | 8/2009 | Amirouche et al. |
| 7,615,055 | B2 | 11/2009 | Disilvestro et al. |
| 7,632,283 | B2 | 12/2009 | Heldreth |
| 7,931,690 | B1 | 4/2011 | Bonutti |
| 8,197,489 | B2 | 6/2012 | Chessar |
| 8,337,508 | B2 | 12/2012 | Lavallee |
| 8,491,589 | B2 | 7/2013 | Fisher |
| 8,562,617 | B2 | 10/2013 | Chessar |
| 8,597,210 | B2 | 12/2013 | Sherman |
| 8,721,568 | B2 | 5/2014 | Rock |
| 9,782,249 | B2 | 10/2017 | Hauri |
| 10,321,904 | B2 | 6/2019 | Plaskos |
| 10,729,417 | B2 | 8/2020 | Cole |
| 11,344,352 | B2 | 5/2022 | Kitch |
| 2004/0019382 | A1 | 1/2004 | Amirouche et al. |
| 2005/0234332 | A1 | 10/2005 | Murphy |
| 2007/0244488 | A1 | 10/2007 | Metzger |
| 2009/0018544 | A1 | 1/2009 | Heavener |
| 2010/0198275 | A1 | 8/2010 | Chana |
| 2010/0249789 | A1 | 9/2010 | Rock et al. |
| 2016/0278754 | A1 | 9/2016 | Todorov et al. |
| 2020/0305943 | A1 | 10/2020 | Hedley et al. |

FOREIGN PATENT DOCUMENTS

| | | | |
|---|---|---|---|
| WO | 20090039346 | A1 | 3/2009 |
| WO | 20160147153 | A1 | 9/2016 |

OTHER PUBLICATIONS

Viskontas, et al: "Computer-Assisted Gap Equalization in Total Knee Arthroplasty", The Journal of Arthroplasty, Churchill Livingstone, Amsterdam, NL, vol. 22, No. 3, Mar. 30, 2007 (Mar. 30, 2007), pp. 334-342, XPO22005028, ISSN: 0883-5403, DOI: 10.1016/J. Arth. 2006.05.018 The Whole Document.

Matsuda, Shuichi et al: "Ligament Balancing in Total Knee Arthroplasty-Medial Stabilizing Technique", Asia-Pacific Journal of Sports Medine, Arthroscopy, Rehabilitation and Technology, vol. 2, No. 4, Oct. 1, 2015 (Oct. 1, 2015), pp. 108-113, XPO55464114, ISSN: 2214-6873, DOI: 10.1016/J.ASMART.2015.07.002 The Whole Document.

Joseph, J, et al; "The Use of Navigation to Achieve Soft Tissue Balance in Total Knee Arthroplasty—A Randomized Clinical S", The Knee, Elsevier, Amsterdam, ML, vol. 20, No. 6, Jul. 26, 2013 (Jul. 26, 2013), pp. 401-406, XPO28770328, ISSN: 0968-0160, DOI: 10.1016/J.KNEE.2013.06.007 The Whole Document.

PCT Search Report From Corresponding PCT Application No. PCT/EP2021/054474, Dated May 10, 2021 (May 10, 2021), 19 Pages.

Heesterbeck, et al: "Patient-Related Factors Influence Stiffness of the Soft Tissue Complex During Intraoperative Gap Balancing in Cruciate-Retaining Total Knee Arthroplasty", Knee Surgery, Sports Traumatology, Arthroscopy, vol. 25 (9) 2017, Published Online Jul. 15, 2015, P.J.C., pp. 2760-2768.

Manning, W.A., et al: "A Load-Measuring Device Can Achieve Fine-Tuning of Mediolateral Load at Knee Arthroplasty but May Lead to a More Lax Knee State", Knee Surgery, Sports Traumatology, Arthroscopy, vol. 27 (7) 2019, Published Online Oct. 4, 2018, pp. 2238-2250. Force Measurements at Various Angles of Flexion.

GB Search Report for Corresponding GB Application No. GB2002918.7, Dated Aug. 11, 2020, 2 Pages.

Athwal, et al; "Lateral Soft-Tissue Structures Contributed to Cruciate-Retaining Total Knee Arthroplasty Stability." Journal of Orthopaedic Research 2017, 35(9), pp. 1902-1909. https://doi.org10.1002/jor.23477.

Athwal, et al; "The Superficiial Medial Collateral Ligament is the Primary Medial Restraint to Knee Laxity After Cruciate-Retaining or Posterior-Stabilised Total Knee Arthroplasty: Effects of Implant Type and Partial Release." Knee Surgery, Sports Traumatology, Arthroscopy 2016, 24(8), pp. 2646-2655. https://doi.org.10.1007/s00167-015-3796-0.

Athwal, et al; "An in Vitro Analysis of Medial Structures and a Medial Soft Tissue Reconstruction in a Constrained Condylar Total Knee Arthroplasty". Knee Surgery, Sports Traumatolgy, Arthroscopy 2016, 25(8), pp. 2646-2655. https://doi.org.10.1007/s00167-016-4087-0.

Cas Ligament Tensor, Surgical Technique, Depuy International LTD., (2005), 16 Pages, Cat. No. 9111-11-124 Version 1, Issued Sep. 2005.

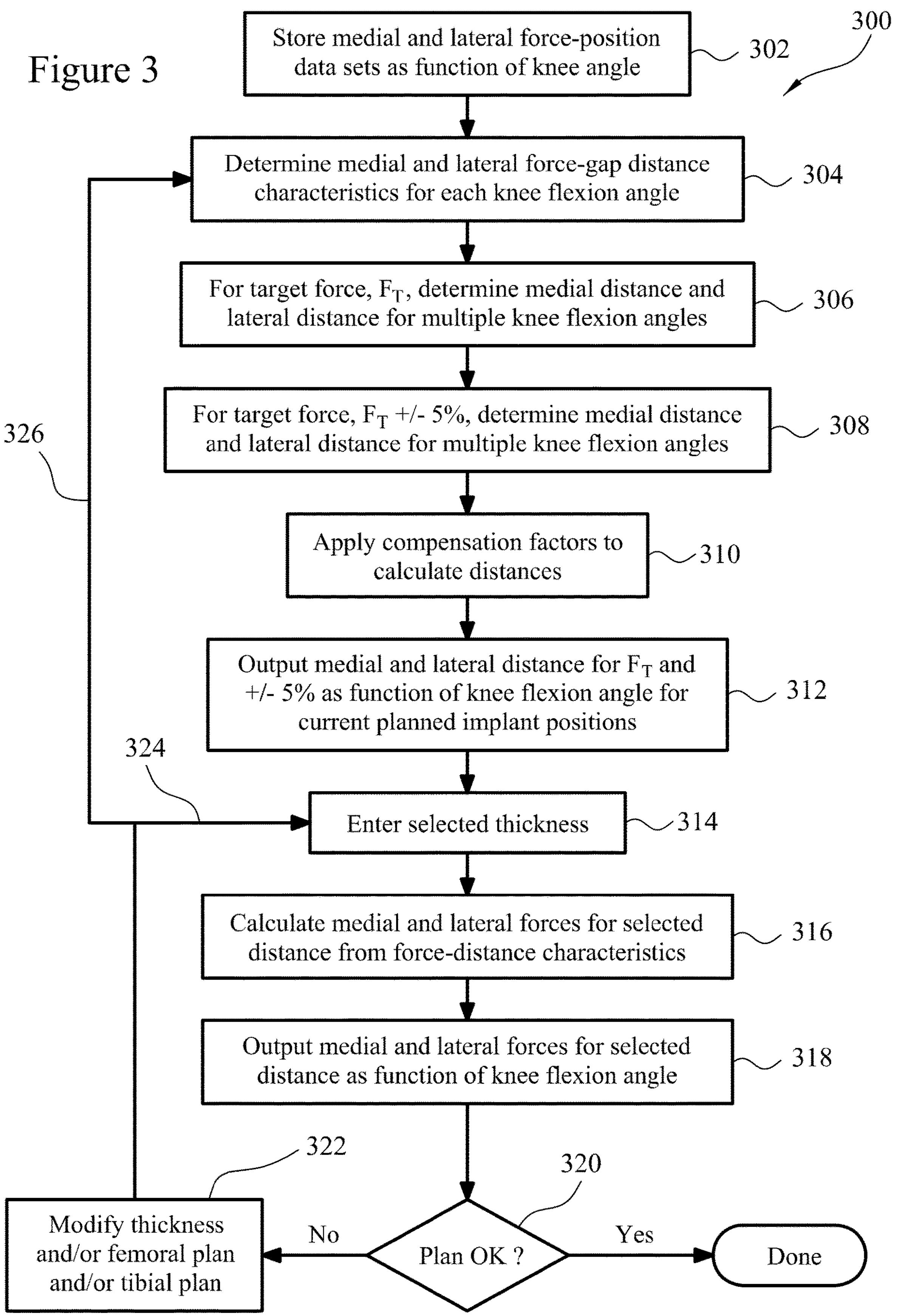

Figure 3
300
Store medial and lateral force-position data sets as function of knee angle
302
Determine medial and lateral force-gap distance characteristics for each knee flexion angle
304
For target force, $F_T$, determine medial distance and lateral distance for multiple knee flexion angles
306
For target force, $F_T$ +/- 5%, determine medial distance and lateral distance for multiple knee flexion angles
308
Apply compensation factors to calculate distances
310
Output medial and lateral distance for $F_T$ and +/- 5% as function of knee flexion angle for current planned implant positions
312
Enter selected thickness
314
Calculate medial and lateral forces for selected distance from force-distance characteristics
316
Output medial and lateral forces for selected distance as function of knee flexion angle
318
Plan OK ?
320
Yes
Done
No
Modify thickness and/or femoral plan and/or tibial plan
322
324
326

Figure 4
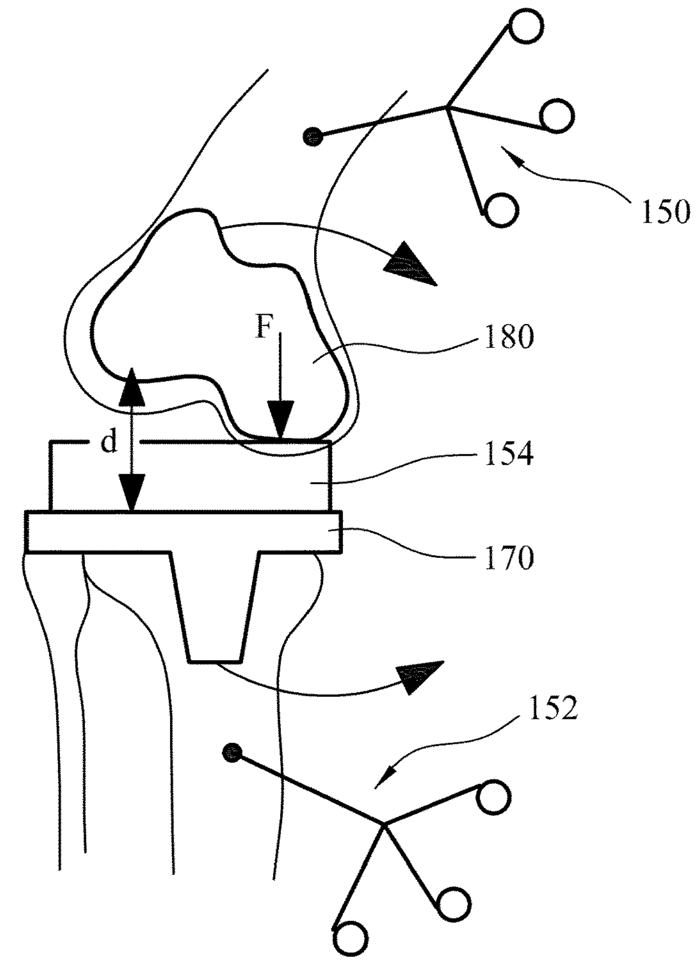
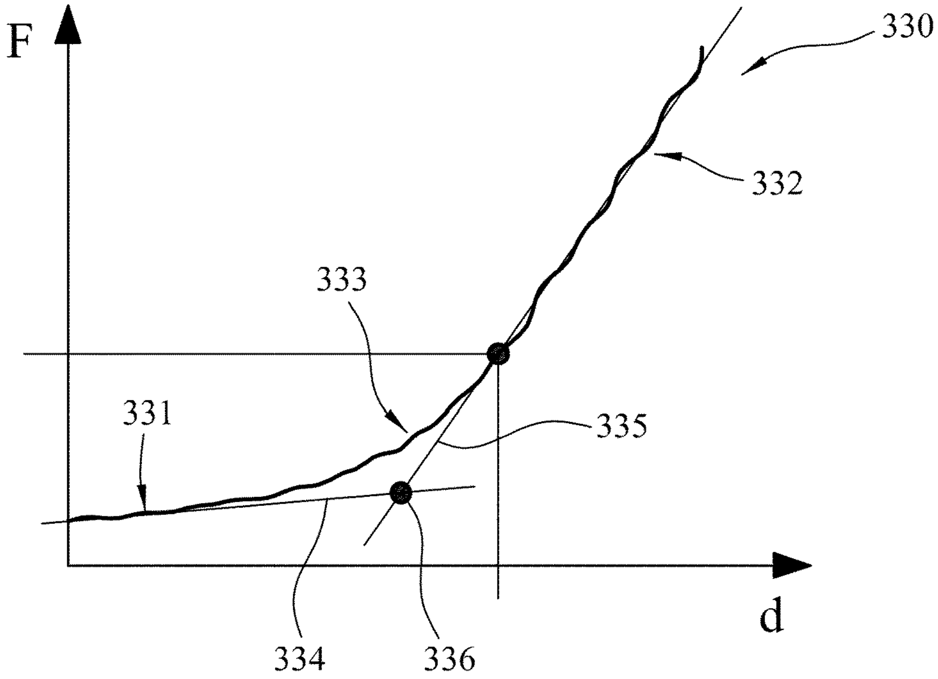
Figure 5

SOFT TISSUE BALANCING IN KNEE REPLACEMENT

The present application claims priority to PCT/EP2021/054474, filed on Feb. 23, 2021, which claims priority to UK Patent Application No. 2002918.7, filed on Feb. 28, 2020, both of which are incorporated in their entireties by reference herein.

TECHNICAL FIELD

The present disclosure invention relates to data processing apparatus, data processing methods and methods for use in knee replacement surgical procedures.

BACKGROUND

Knee replacement surgery or knee arthroplasty is a generally well known surgical procedure in which one compartment (unicompartmental knee arthroplasty or partial knee replacement) or the whole of the knee (total knee replacement) is replaced by prosthetic implants typically including a femoral component and a tibial component. The femoral component is attached to the distal end of the femur and generally replaces the femoral condyles. The tibial component is attached to the proximal end of the tibia and generally replaces the tibial plateau.

An important feature of knee arthroplasty generally is the size, position and orientation of the prosthetic components. This generally involves determining the positions and orientations of the various cuts made to resect the distal femur and the proximal tibia and is generally known in the art.

A further important feature of knee arthroplasty is management of the soft tissues that surround the knee and which can be an important aspect the surgical outcome for the patient. During some knee procedures, some of the native soft tissue structures may be sacrificed as part of the surgical procedure, such as the anterior cruciate ligament or posterior cruciate ligament. In some instances, surgeons may perform soft tissue release to reduce the tension in the soft tissues so as to improve the overall performance of the knee joint. Additionally or alternatively, surgeons may adjust bone cut positions to take up some of the laxity that would otherwise be present in the soft tissue structures.

However, the knee joint is not purely a simple pivot about a constant axis of rotation and involves quite a complex relative movement between the articulating surfaces of the femur and tibia and which there is a complex interaction of the various forces exerted on the knee by the various soft tissue structures.

Hence, apparatus and methods which help take into account the soft tissue structures of the knee during replacement knee surgery would be beneficial.

A first aspect of the disclosure provides a data processing method carried out by a data processing apparatus and comprising: storing measured medial knee gap data items and first measured resulting force data items and measured lateral knee gap data items and second measured resulting force data items for a plurality of knee flexion angles; determining a lateral force-distance characteristic for each of the plurality of knee flexion angles; determining a medial force-distance characteristic for each of the plurality of knee flexion angles; using the lateral force-distance characteristic to determine a lateral knee gap distance corresponding to a target force for at least one of the plurality of knee flexion angles; using the medial force-displacement characteristic to determine a medial knee gap distance corresponding to a target force for at least one of the plurality of knee flexion angles; and outputting the lateral knee gap distance corresponding to the target force and the medial knee gap distance corresponding to the target force as a function of knee flexion angle.

Outputting may comprise outputting in a visual form and in particular in a graphical form, for example by displaying one or more graphs.

The target force may be a pre-selected value. For example, the target force may be in the range of 50 Newtons to 150 Newtons or more preferably in the range of 80 Newtons to 120 Newtons.

The target force may be determined from the lateral force-distance characteristic and/or from the medial force-distance characteristic.

The target force may be based on a crossover force at which the force-distance characteristics changes from a first behaviour to a second behaviour. The target force may be the cross over force or may be at least 110% of the cross over force or may be less than 90% of the cross over force. The target force may lie with the second behaviour of the force-distance characteristic.

The data processing method may further comprise: using the lateral force-distance characteristic to determine a variation in lateral knee gap distance corresponding to a variation in the target force for at least one of the plurality of knee flexion angles; using the medial force-displacement characteristic to determine a variation in medial knee gap distance corresponding to a variation in the target force for at least one of the plurality of knee flexion angles; and outputting the variation in lateral knee gap distance with the lateral knee gap distance and/or the variation in medial knee gap distance with the medial knee gap distance.

The data processing method may further comprise: receiving a thickness of a planned tibial component; determining the planned lateral knee gap and the planned medial knee gap arising from the thickness of the planned tibial component as a function of knee flexion angle; using the lateral force-distance characteristic to determine a predicted lateral force corresponding to the planned lateral knee gap as a function of knee flexion angle; using the medial force-distance characteristic to determine a predicted medial force corresponding to the planned medial knee gap as a function of knee flexion angle; and outputting the predicted lateral force and the predicted medial force as a function of knee flexion angle.

The predicted lateral force as a function of knee angle and/or the predicted medial force as a function of knee flexion angle may be output together with the output of the lateral knee gap distance corresponding to the target force and the medial knee gap distance corresponding to the target force as a function of knee flexion angle.

The data processing method may further comprise receiving a further thickness of the planned tibial implant, and repeating the method steps using the further thickness.

The data processing method may further comprise: receiving a modified plan for a femoral component and/or tibial component; and repeating the method using the modified plan for the femoral component and/or tibial component.

The data processing method may further comprise compensating the lateral knee gap distance to correspond to a lateral knee gap distance for a knee having tension in the medial ligaments and the lateral ligaments and/or compensating the medial knee gap distance to correspond to a medial knee gap distance for a knee having tension in the medial ligaments and the lateral ligaments.

The measured medial knee gap data items and/or the measured lateral knee gap data items may be derived from tracking data received from a tracking system.

The first measured resulting force data items and/or the second measured resulting force data items may be derived from measurements received from a knee tensioner.

The first measured resulting force data items and/or the second measured resulting force data items may be derived from measurements received from an electronic force senor.

In some embodiments, using the lateral force-distance characteristic to determine the lateral knee gap distance corresponding to a target force for at least one of the plurality of knee flexion angles may include:

a. determining from the lateral force-distance characteristic for at least one knee flexion angle that a stiffness threshold is met or exceeded; and
b. in response to the determination that the stiffness threshold is met or exceeded, setting the lateral knee gap distance for that knee flexion angle to a value that is a predetermined amount less than a measured lateral knee gap associated with a maximum force contained in the measured lateral knee gap data items and the force data items data items for that knee flexion angle.

In some embodiments, using the medial force-distance characteristic to determine the medial knee gap distance corresponding to a target force for at least one of the plurality of knee flexion angles may include:

a. determining from the medial force-distance characteristic for at least one knee flexion angle that a stiffness threshold is met or exceeded;
b. in response to the determination that the stiffness threshold is met or exceeded, setting the medial knee gap distance for that knee flexion angle to a value that is a predetermined amount less than a measured medial knee gap associated with a maximum force contained in the measured medial knee gap data items and the force data items data items for that knee flexion angle.

A second aspect of the disclosure provides a non-transitory computer readable medium storing instructions executable by a data processor to carry out the data processing method of the first aspect.

A third aspect of the disclosure provides a data processing apparatus comprising: a processor; and the non-transitory computer readable medium of the second aspect.

A fourth aspect of the disclosure provides a computer assisted surgery system including the data processing apparatus of the third aspect.

The computer assisted surgery system may further comprise: a tracking system; and/or a surgical robot; and/or a knee force sensor.

A fifth aspect of the disclosure provides a method comprising measuring a lateral force-distance characteristic and a medial force-distance characteristic of a knee of a patient at a plurality of knee flexion angles; determining a lateral knee gap corresponding to a lateral target force as a function of knee flexion angle from the lateral force-distance characteristics; determining a medial knee gap corresponding to a medial target force as a function of knee flexion angle from the medial force-distance characteristics; and using the medial knee gap and the lateral knee gap as a function of knee flexion angle to assess a knee gap arising from a planned knee replacement procedure to be carried out on the knee of the patient.

The lateral target force and/or the medial target force may be a pre-selected target force.

The lateral target force may be determined from the lateral force-distance characteristic and/or the medial target force may be determined from the medial force-distance characteristic.

The lateral target force may be based on a lateral cross over force corresponding to a change of the lateral force-distance characteristic of the knee from a first behaviour to a second behaviour and/or the medial target force may be based on a medial cross over force corresponding to a change of the medial force-distance characteristic of the knee from a first behaviour to a second behaviour.

The lateral target force may be the lateral cross over force and/or the medial target force may be the medial cross over force.

The lateral target force may be greater than the lateral cross over force and/or the medial target force may be greater than the medial cross over force.

The lateral target force may be a predetermined percentage of the lateral cross over force and/or the medial target force may be a predetermined percentage of the medial cross over force. For example, the predetermined percentage may be 80%, 90%, 110%, 120% or 130%. The predetermined percentage may be at least 110%. The predetermined percentage may be less than 90%.

The plurality of knee flexion angles may include at least three, five, seven or nine different knee flexion angles. The plurality of knee flexion angles may include at least a flexion angle, an extension angle and an angle between flexion and extension.

The plurality of knee flexion angles may fall within the range of at least −10 to 120 degrees or at least −10 to 90 degrees or at least 0 to 90 degrees.

The method may further comprise inserting a tension meter into the knee of the patient between the proximal tibia and a one of the medial and the lateral condyles; using the tension meter to vary the tension in at least a collateral ligament of the knee adjacent the tensioner; and measuring the distance between the femur and the tibia and the force applied to at least the collateral ligament of the knee as the tension is varied.

The method may further comprise: inserting an electronic force sensor into the knee of the patient between the proximal tibia and a one of the medial and the lateral condyles; moving the tibia in a one of the medial and the lateral direction in the coronal plane to vary the tension in the other of the medial and the lateral ligaments of the knee; and measuring the other of the medial and the lateral distance between the femur and the tibia and the force detected by the electronic force sensor as the tension is varied.

The method may further comprise: tracking the position of the femur and the position of the tibia of the patient; determining the knee flexion angle from the tracked position of the femur and the tracked position of the tibia; and/or determining the lateral distance between the distal femur and the proximal tibia from the tracked position of the femur and the tracked position of the tibia; and/or determining the medial distance between the distal femur and the proximal tibia from the tracked position of the femur and the tracked position of the tibia.

The method may further comprise: displaying the medial knee gap and the lateral knee gap as a function of knee flexion angle.

The method may further comprise: using the lateral force-distance characteristic to determine a variation in lateral knee gap corresponding to a variation in the target force for a plurality of knee flexion angles; using the medial force-displacement characteristic to determine a variation in medial knee gap corresponding to a variation in the target force for a plurality of knee flexion angles; and displaying the variation in lateral knee gap with the lateral knee gap and/or the variation in medial knee gap with the medial knee gap.

The variation may be a pre-selected percentage of the target force. The size of the variation may be 10% or 20%. The variation may be 105% and 95% of the target force or 110% and 90% of the target force.

The method may further comprise: inputting a planned tibial component thickness; using the lateral force-distance characteristic to determine a predicted lateral force corresponding to the planned tibial component thickness as a function of knee angle; using the medial force-distance characteristic to determine a predicted medial force corresponding to the planned tibial component thickness as a function of knee angle; and displaying the predicted lateral force and the predicted medial force as a function of knee angle.

The method may be carried out using a computer assisted surgery system. The computer assisted surgery system may be used to carry out the planned knee replacement procedure on the patient.

The method may include:

a. determining from the lateral force-distance characteristic for at least one knee flexion angle that a stiffness threshold is met or exceeded at that knee flexion angle; and
b. in response to said determination that the stiffness threshold is met or exceeded, determining the lateral knee gap corresponding to the lateral target force for that knee flexion angle to be a value that is a predetermined amount less than a measured lateral knee gap associated with a maximum measured lateral force in the lateral force-distance characteristic for that knee flexion angle.

The method may include:

a. determining from the medial force-distance characteristic for at least one knee flexion angle that a stiffness threshold is met or exceeded for that knee flexion angle; and
b. in response to said determination that the stiffness threshold is met or exceeded, determining the medial knee gap corresponding to the medial target force for that knee flexion angle to be a value that is a predetermined amount less than a measured medial knee gap associated with a maximum measured medial force in the medial force-distance characteristic for that knee flexion angle.

The computer assisted surgery system may include a surgical robot. The surgical robot may be used to carry out at least some of the planned knee replacement procedure on the patient.

BRIEF DESCRIPTION OF THE DRAWINGS

Embodiments will now be described in greater detail, and by way of example only, and with reference to the accompanying drawings, in which:

a.

b.

c. FIG. 3 shows a process flow chart illustrating a data processing method according to a third embodiment;

d. FIG. 4 shows an illustration of a knee joint under a varus load and including the planned positions of femoral and tibial implants e. FIG. 5 shows a first graph illustrating a measured force-distance characteristic of a knee joint at a particular knee angle;

f.

g.

h.

i.

j.

k.

l.

m.

n.

o. |

p.

q.

r.

s.

t.

u.

v.

w.

DETAILED DESCRIPTION OF THE DRAWINGS

Figure 1:
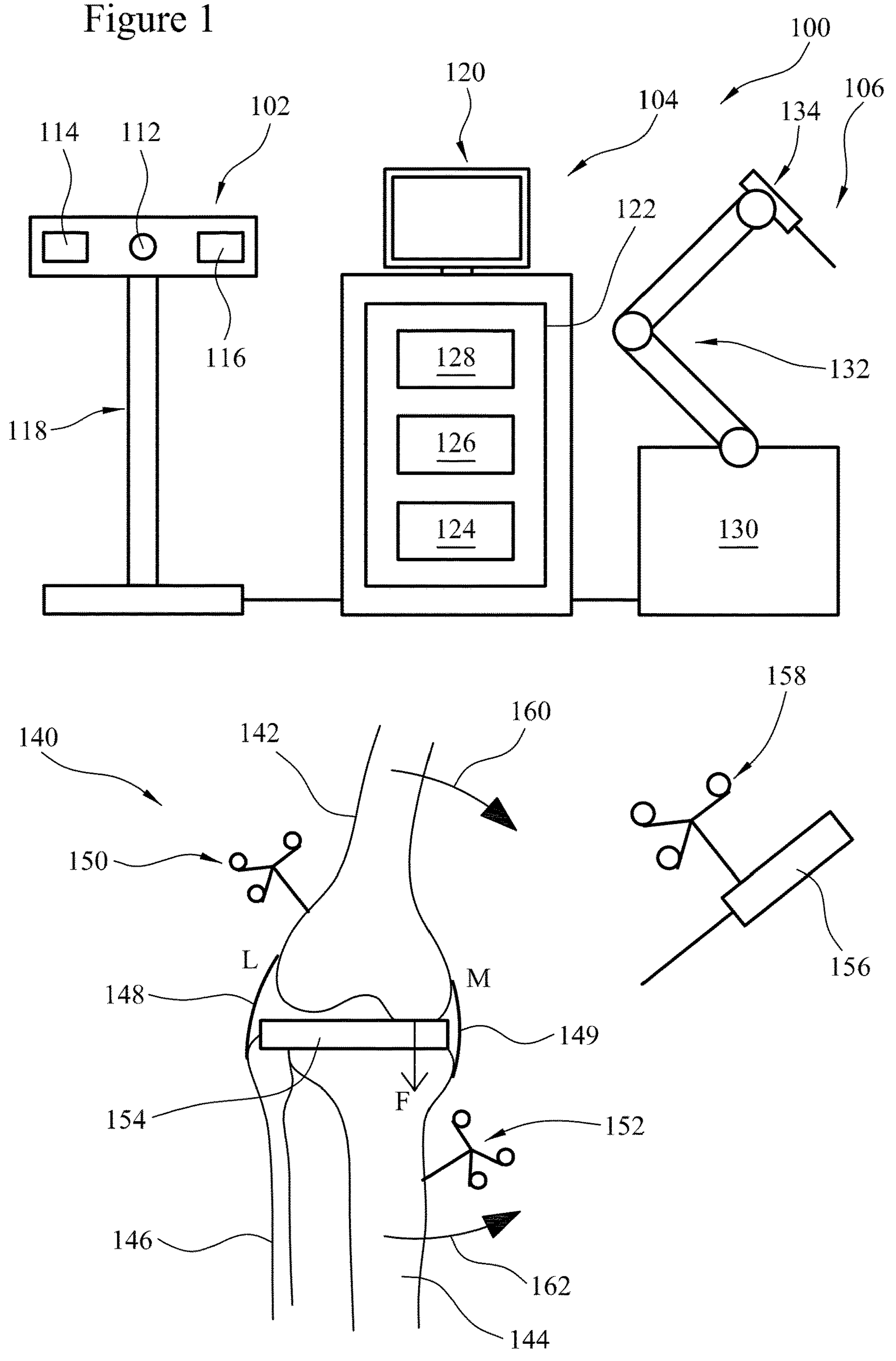
FIG. 1 shows a schematic block diagram of a system including data processing apparatus according to a first embodiment.

In the Figures of drawings, the same reference numerals are used to refer to like items unless indicated otherwise.

With reference to FIG. 1 there is shown a schematic block diagram of a computer assisted surgery (CAS) system 100 which may include various apparatus and which may carry out various data processing methods or be used to carry out various surgical methods. The CAS system 100 may include a tracking system 102, a data processing system 104 and, optionally, a surgical robot 106. Although illustrated as separate subsystems in FIG. 1, it will be appreciated that tracking system, data processing system and robotics system 106 may be integrated into a single CAS system.

In the illustrated embodiment, the tracking system 102 is provided in the form of an infrared optical tracking system including one or more sources of infrared radiation 112, a pair of mutually spaced infrared cameras, 114, 116, mounted on a support 118. However, other wired and wireless tracking systems are also generally known in the art and may utilise, for example, acoustic, magnetic, light or other radiation based tracking technologies. However, simply for the sake of clarity of explanation, an infrared wireless tracking system will be described. The tracking system 102 is in communication with the data processing system 104 which may also implement some of the functionality of the tracking system.

The data processing system 104 includes substantially conventional data processing apparatus, including one or more data processors, memory and storage devices together with various communication buses, power supplies, communication interfaces and user input/output interfaces and devices. The data processing apparatus is configured by suitable software stored in memory to carry out various operations as described in greater detail below. As schematically illustrated in FIG. 1, the data processing system 104 includes a display 120. Display 120 may display various images from a data and graphics to the user during use. In some embodiments, display 120 may be a touch screen device to provide user input to control operation of the CAS system 100.

The data processing system 104 illustrated in FIG. 1 is purely schematic and in practice may be implemented using a general purpose computer with suitable software. The physical form of the general purpose computer is not limited and may include portable and/or hand held devices including, for example, tablets and smart phones. In some embodiments one or more cameras may be provided integrally to the general purpose computer to provide image based tracking, rather than using a separate tracking system as illustrated in FIG. 1.

Data processing system 104 includes software 122 which may include one or more software modules as schematically illustrated in FIG. 1. The CAS system 104 may include tracking software which receives data and/or tracking signals from the tracking system and converts those into position and/or orientation data specifying the position and/or orientation of various items tracked by the tracking system within a common reference frame of the tracking system. The position and/or orientation data may be passed by the tracking software subsystem to other parts of the CAS system as required. The CAS software 122 may include a workflow software module 124 which controls the overall operation and workflow of the CAS system 100. The workflow software module 124 may be used to select a surgical procedure to be carried out, a particular version of that surgical procedure and also various modifications or specific instances of a surgical procedure.

A planning software module 126 may also be provided by which the user may plan various aspects of the surgical procedure. For example, for an orthopaedic surgical procedure, this may include planning the type of implant to be used, the size of the implant, a position and/or orientation of the implant and the position and/or orientation of various cuts to be made to the bones of the patient in order to implement the surgical plan. In other instances, planning may be carried out on a separate application and the planning data imported to the CAS system over a network connection or similar.

The software 122 may also include a registration software module 128 which receives tracking data from the tracking system in order to register the position of the patient's bones within the reference frame of the tracking system. Registration is generally known in the art and is not described in the greater detail herein.

As also illustrated in FIG. 1, the CAS system 100 may optionally include a surgical robot 106. Surgical robot 106 includes a base 130 including various electronic controls, interface and power systems. An articulating limb or arm 132 is attached to the base 130 and includes an end effector or instrument 134. Multiple articulating limbs may be provided. The surgical robot 106 may be controlled by the data processing system 104 in order to carry out one or more steps of the surgical procedure and control of the surgical workflow software 124 and a user.

As also illustrated in FIG. 1, there is shown a right knee joint 140 of a patient including the femur 142, tibia 144 and fibula 146. The patella is omitted for the sake of clarity. Also schematically illustrated are the lateral collateral ligaments 148 and the medial collateral ligaments 149. A first reference array 150 including an arrangement of three infrared reflective spheres is shown attached to the femur. A second reference array 152 similar to the first, is shown attached to the tibia. Also illustrated in FIG. 1 is an electronic force sensor device 154 described in greater detail below. Also illustrated in FIG. 1 is a pointer instrument 156 bearing a third reference array 158. Trackable pointer 156 can be used to capture the position of various anatomical features of the patient's knee during the surgical procedure as generally known in the art.

Figure 2:
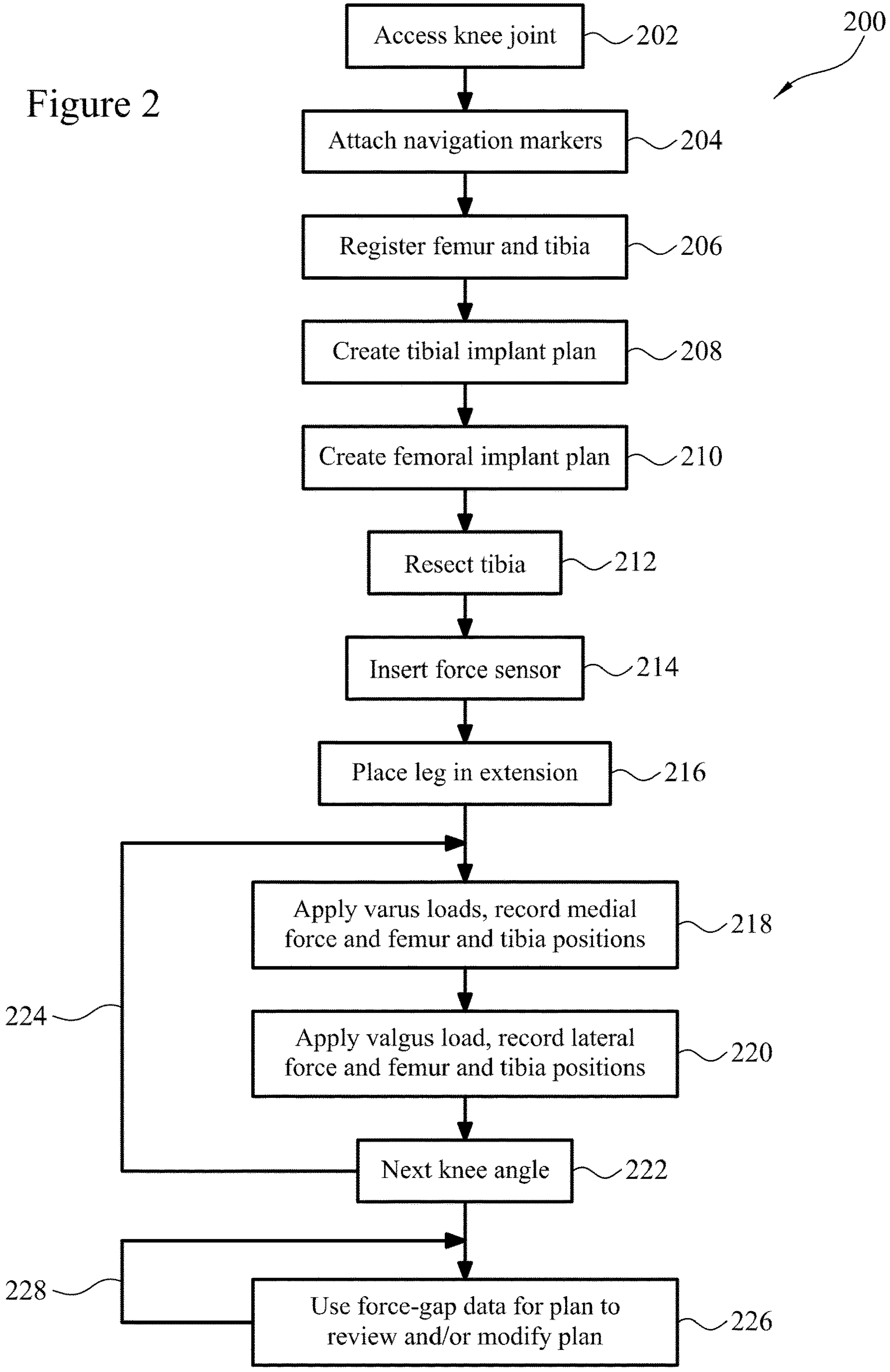
FIG. 2 shows a flow chart illustrating a method according to a second embodiment.

FIG. 2 shows a flow chart illustrating a method 200. Method 200 is used to generate knee gap versus force data for the patient's knee as a function of knee angle. At 202, the surgeon creates access to the knee joint. At 204, a first navigation marker 150 is attached to the femur and a second navigation marker 152 is attached to the tibia 144. These allow the position of the femur and the tibia to be tracked during the surgical procedure. The navigation markers may also be attached to the tibia and femur before creating access to the knee joint, via simple incisions though the patient's skin.

At 206 the femur and the tibia are registered within the reference frame of the tracking system. For example, the surgeon may use the trackable pointer to register the position of various anatomical points of the femur relative to the femoral marker 150 and various anatomical points of the tibia relative to the tibial marker 152. For example, the positions of the centre of the distal femur and the position of the femoral head may be registered and used to define the femoral mechanical axis. The anterior of the femur, the most distal points of the medial and lateral condyles and the most posterior points of the medial and lateral condyles may also all be registered. For the tibia, the centre of the proximal tibia and the tibial malleoli may be registered and used to define the tibial mechanical axis.

Also, the anterior-posterior axis of the tibia can be registered by positioning the trackable pointer stationary and pointed in a direction parallel to the anterior-posterior axis of the tibia so as to define the anterior posterior axis. The sagittal plane is then defined by having the mechanical axis of the tibia lying on it and also being parallel to the registered anterior-posterior axis of the tibia. This sagittal plane of the tibia allows the system to distinguish between pure flexion-extension angles and varus-valgus angles in which the mechanical axis of the tibia is tilted out of the sagittal plane.

Also, the most distal point on the medial and lateral tibial condyles and the direction of the tibial anterior/posterior axis may all be registered.

In other embodiments, in which a detailed 3D image of the knee is available, e.g. from a CT scan, then the CT scan images can be used instead and the knee registration may be carried out by registering the CT scan to the patients knee bones in a manner generally known to a person of ordinary skill in this art.

Then at 208, the planning software module 126 may then be used to plan an initial tibial cut. The initial tibial cut plan is known relative to the position of the tibial array and hence the planned position can be determined as the tibia is moved by tracking the tibial array. For example, the tibial cut plan may define the planned initial tibial cut as being perpendicular to the tibial mechanical axis in the coronal view, a three degree posterior slope in the sagittal view and a 9 mm resection level from the most proximal condyle.

Then at 210, the planning software module 126 may be used to plan a first femoral implant position. The first femoral implant plan is known relative to the position of the femoral array and hence the planned position of the femoral component can be determined as the femur is moved by tracking the femoral array. For example, the first femoral implant plan may define the femoral implant being positioned perpendicular to the femoral mechanical axis, 3 degrees of external rotation relative to the posterior condyle points, an implant size and anterior-posterior position to restore the medial condyle and minimise overhand and/or notching anteriorly, and a 9 mm resection from the most prominent distal condyle.

Then at 212 the tibial resection is performed. In particular the tibia is resected according to the tibial plan created previously. This may include navigation of instruments such as a tibial cutting block. Additionally or alternatively, this may include controlling the robotic arm 132 to position and use a saw, burr or some other end effector to resect the tibia.

At 214, an electronic force sensor 154 is inserted into the gap and secured to the resected tibia. Ideally the force sensor has a thickness equivalent to the thickness of tibial bone that has been removed/ Hence, the force sensor acts as a spacer and essentially recreates the native tibia. In other embodiments, in which a film force sensor is used, the tibial does not need to be resected first, and the film force sensor may simply be inserted in the knee between the femur and tibia and secured to the native surface of the tibia.

The electronic force sensor 154 can measure the force applied to it and transmit force data via a wired or wireless connection to the data processing system 104. As described in greater detail below, the electronic force sensor 154 is used to measure medial and lateral forces as a function of medial and lateral gap distances over a range of flexion angles of the knee joint.

At 216, the patient leg is placed in a first flexion angle corresponding to full extension (i.e. 0° flexion). Then, at 218, the surgeon applies an increasing varus moment to the knee joint in full extension by tilting the tibia medially relative to the femur within the coronal plane. This is illustrated by arrows 160, 162, in FIG. 1. As also illustrated in FIG. 1, application of a varus load causes the lateral ligaments 148 to lengthen and the medial condyle exerts a force on the force sensor 154. As the varus moment is increased, the tracking system tracks the motion of the femoral array and the tibial array as a function of time so that the relative movement of the femur and tibia can subsequently be determined. At the same time, the output of the force sensor is recorded also as a function of time so that the force as a function of the femoral array and tibial array positions can be determined.

Then, at 220, the preceding step is repeated but while applying an increasing valgus moment to the knee joint, by moving the tibia in a lateral direction relative to the femur within the coronal plane. Similarly to 218, the force output by the sensor and the position of the femoral and tibial markers are tracked to provide force, tibial position and femoral position data as a function of time.

At 222, a next knee flexion angle is selected. For example, with full extension corresponding to 0° flexion, then the knee angle may be increased by, for example, 15°, to provide a 15° flexion knee angle. For this new knee angle, as illustrated by process flow line 224, the method returns and for the new knee flexion angle, further sets of force-position data values are recorded by applying varus and valgus moments respectively within the coronal plane of the tibia. The method then repeats at increasing knee flexion angle values until a maximal flexion angle is arrived at, for example, sets of data may be recorded for flexion angles of 0°, 15°, 30°, 60°, 90° and 120°.

After the force-position data has been measured for the patient's knee as a function of knee flexion angle, and captured by the data processing system 104, the data processing system 104 can carry out various data processing operations, described in greater detail below. Graphical representations of the results of the data processing can then be output via the display device 120 for viewing by the surgeon. In particular, as described in greater detail below, the data processing system 104 may display one or more graphical indications of the medial and lateral knee gap value as a function of knee angle for a predetermined medial force and lateral force. This force-gap data may be used by the surgeon to assess or review and/or modify one or more planned properties of the surgical plan in order to arrive at an acceptable knee gap as illustrated by step 226 in FIG. 2. As also illustrated in FIG. 2, the display data may be updated if the surgeon modifies an initial plan and the data redisplayed to allow iterative planning as illustrated by return line 228.

With reference to FIG. 3, there is shown a flow chart illustrating a data processing method 300 carried out by the data processing system 104 of the CAS system 100. As described above, medial force-position data sets and lateral force-position data sets are measured and stored at 302 by the data processing system 104 during method 200. As a preliminary operation, at 302 the CAS system may also calculate the knee flexion angle from the femoral marker tracking data, the tibial marker tracking data and the registered femoral mechanical axis, the registered sagittal plane of the tibia and the registered tibial mechanical axis as being the angle subtended between the femoral mechanical axis and the tibia mechanical axis within the sagittal plane of the tibia at the time that a force is measured and a force data item is stored. At 304, from the stored force-position data sets, a force-distance function is determined for each knee flexion angle for the lateral side of the knee and also for the medial side of the knee.

For example, and with reference to FIG. 4, for a first knee flexion angle, e.g. 0°, the minimum distance, d, perpendicular to the between the planned tibial cut and the lateral condyle of the first planned femoral position is determined. The distance d may be determined from the tibial plan and the tracking data for the tibial marker, and the first femoral plan and the tracking data for the femoral marker, which can be used to determine the relative positions of a model of the tibial implant 170 and a model of the femoral implant 180. The force data is correlated with the tracking data by time and therefore the recorded force for that distance, d, can be determined. Hence, for each time point of the recorded force data, the distance, d, is determined from the tracking data and planned implant positions.

In other embodiments, if the resected surface of the tibia has been registered, then the minimum distance perpendicular to the resected tibial surface and the lateral condyle of the first planned femoral position may be determined instead.

For example, FIG. 5 shows a plot 330 of the measured force (which may be, for example, in Newtons, but the absolute value is not necessarily important) against the lateral knee gap or distance, d, for a particular knee angle. As illustrated in FIG. 5, the force-distance function has a generally linear first part 331, a second generally linear part 332 and an intermediate crossover region 333. The first linear portion 331 can be approximated by a first straight line fit 334 and the second linear portion 332 can be approximated by a second straight line fit 335. A crossover point may be defined by the intersection 336 of the first straight line fit 334 and second straight line fit 335.

As illustrated in FIG. 5, initially, the soft tissue structures of the knee, including the collateral ligament, exert a relatively low force as the displacement increases. After the changeover region, as the displacement increases, a significantly greater force is exerted by the soft tissue structures. The first region of behaviour 331 generally includes ligament fibres aligning and/or straightening whereas the second region of behaviour 332 generally includes ligament tissues stretching.

Depending on the knee flexion angle various different soft tissue structures of the knee will be involved in resisting the varus and valgus loads. For example in extension, the force-distance function 330 will represent the properties of the posterior capsule, and at some flexion angles, the anterior cruciate ligament (ACL) and/or posteriori cruciate ligament (PCL) may also affect the force-distance function. Hence, depending on the knee flexion angles, the force-distance function will be the result of various soft tissue structures of the knee and/or the result of aggregates of multiple soft tissue structures, including, but not limited to, the collateral ligaments.

Further, when multiple soft tissue structures are involved, the force-distance characteristic may not have the same shape or form as the "ideal" one illustrated in FIG. 5.

Although FIG. 5 shows a plot of the force-distance data, it is not necessary to plot and output the data. Rather, the force-distance function may be determined by fitting one or more mathematical functions to the recorded data. For example, as illustrated in FIG. 5, the function can be approximated by first 324 and second 335 straight line fits. In other embodiments, a mathematical function, for example a polynomial, having a similar general form to the illustrated plot 330 can be used and parameters varied in order to fit that function to the collected data.

In a similar way, the minimum perpendicular distance, d, between the planned tibial cut and the medial condyle for the first planned femoral implant position is determined for each recorded force value to provide a medial force-distance function.

This is then repeated for each of the knee flexion angles, to provide a medial force-distance function and also a lateral force-distance function for each of the different knee flexion angles.

After the force-distance function for each knee flexion angle, for both the medial and lateral sides, has been determined at 304, at 306, those functions are used to determine the medial and lateral gaps arising for a particular force value for each of the knee flexion angles. The particular force value may be based on some characteristic of the force-distance function for at least one knee flexion angle, or otherwise related to the measured force-distance characteristic, and hence may be patient specific.

For example, with reference to FIG. 5, the particular or target force, $F_T$, may be the crossover force corresponding to the force at which the crossover in behaviour 333 between the first linear region 331 and second liner region 332 of the function occurs, or a force based on that, for example X % greater than the crossover force, e.g. 10% greater. However, in other embodiments an absolute force value may be set and used as the particular force value.

Figure 6:
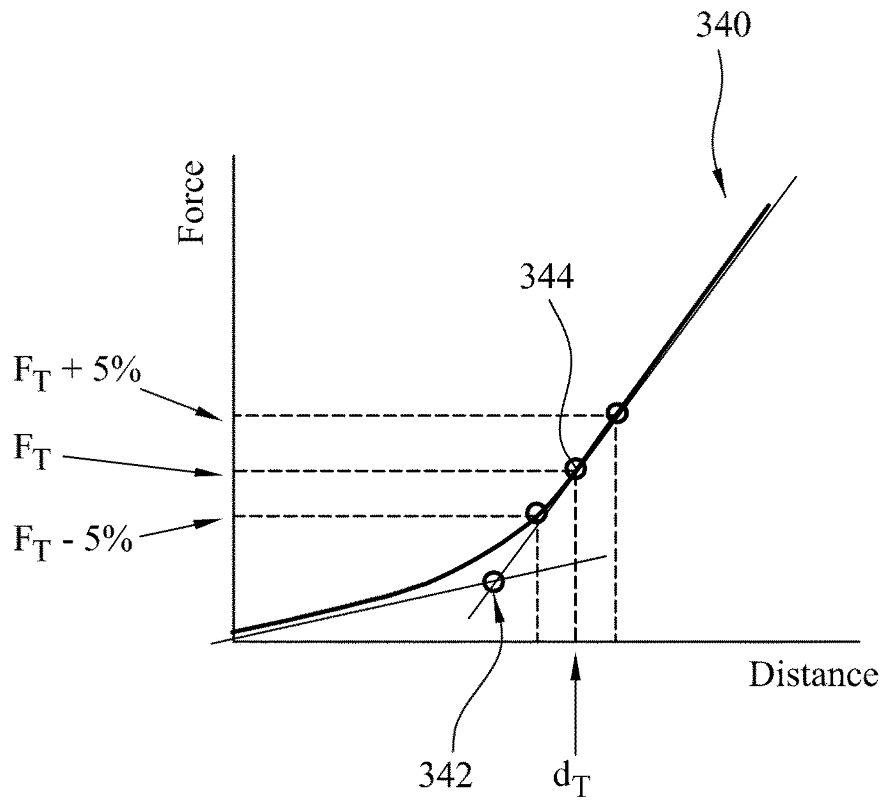
FIG. 6 shows a second graph illustrating a measured force-distance characteristic of a knee joint at a particular knee angle.

As a patient specific force example, FIG. 6 graphically shows a plot of the force-distance function 340 for a knee angle closer to full extension, for example, approximately 30° of flexion. In FIG. 6, the crossover force 342 is shown and the target force value, $F_T$, is set to some % thereof, e.g. $F_T$+10%, and then the distance, $d_T$, corresponding to that target force value is determined from the function 340. Setting $F_T$ to 110% of the cross over force 342 provides some pre-tension to the tissues but also leaves room for further tension to be applied, i.e. the soft tissues are not too tight. As illustrated in FIG. 6, the target force value 344 is set to be in the second linear part of the force-distance characteristic, and in particular after the transition region 342, and toward the beginning of the second linear region.

Optionally, distances corresponding to small changes in the target force $F_T$ may also be calculated and used in a sensitivity assessment as described in greater detail below. For example, as illustrated in FIG. 6, a distance corresponding to $F_T$−5% may be calculated from the function 340 and also a distance corresponding to $F_T$+5% may be calculated from the function 340.

Figure 7:
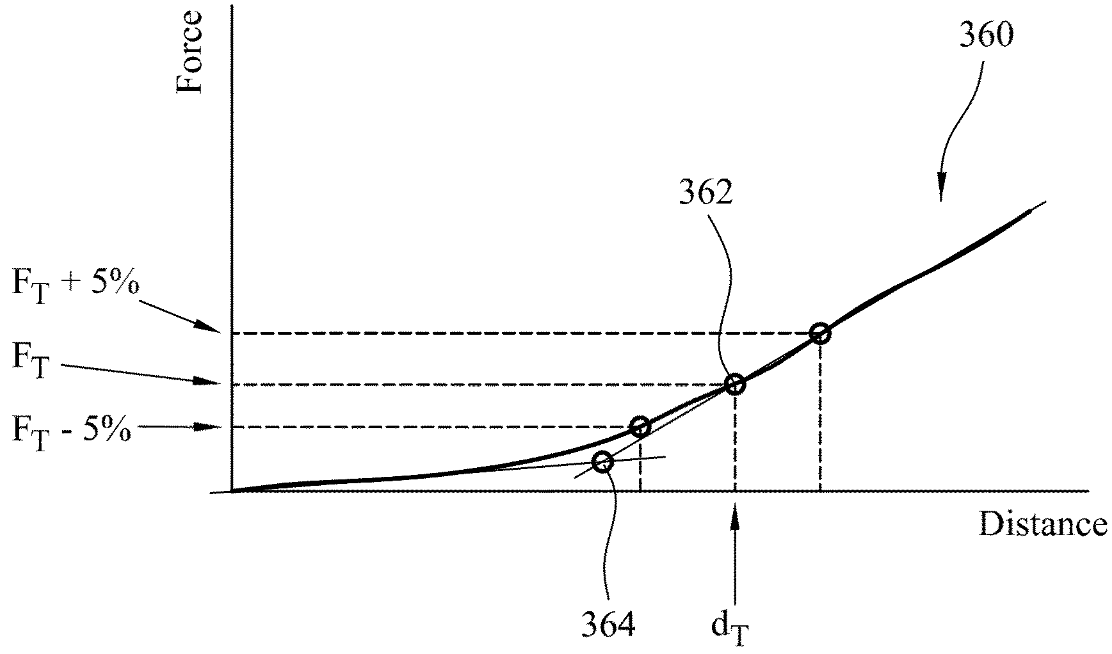
FIG. 7 shows a third graph illustrating a measured force-distance characteristic of a knee joint at a particular knee angle.

Similarly, FIG. 7 shows a lateral force-distance characteristic 360 for a greater knee flexion angle, for example approximately 90° of flexion. Again, a lateral target force value, $F_T$, 362 is set at 110% of the cross over force and the corresponding lateral distance 364 is calculated from the force-distance characteristic 360. Also, optionally, distances corresponding to $F_T$+5% and $F_T$−5% are calculated. As will be apparent from comparing FIGS. 6 and 7 the absolute value of the target force, $F_T$, will vary with knee flexion angle and is not necessarily constant. Hence, similarly, the magnitude of the variation in $F_T$, e.g. $F_T$±5% will also vary.

These calculations may be carried out using the respective force-distance functions for the lateral and the medial sides of the knee and potentially for each of the knee flexion angles as illustrated by processes 306 and 308 in FIG. 3.

However, as discussed above, the force-distance characteristic may not have the ideal form shown in FIGS. 5, 6 & 7 for some knee flexion angles. Also, as illustrated in FIGS. 6 and 7, for different knee flexion angles, $F_T$, may have different values. If there are multiple target forces at multiple flexion angles, then it may not be possible to satisfy all of those simultaneously without a custom implant. Hence, a couple of $F_T$ values may be selected and so as to optimise around those, or some average value of $F_T$ may be used instead. Also, if only some of the force-distance functions have the characteristic form illustrated in FIGS. 5, 6 & 7, then the target distance data, dr, may be obtained from those force-distance functions only, rather than using the force-distance function for every knee angle to try and determine the target distance $d_T$.

Hence, at 306, for several knee angles, the medial gap and the lateral gap for the knee corresponding to target medial and lateral force values have been determined.

Optionally, as illustrated by box 308 of FIG. 3, the sensitivity of the lateral and medial force to gap distance may also be determined at multiple knee angles for which the force-distance characteristic exhibits the desired form to a sufficient extent. Although this is illustrated as a separate step in FIG. 3, it will be appreciated that steps 306 and 308 may easily be combined.

At 310, the medial and lateral distance values calculated previously may be compensated, using a compensation value or function or look up table data or similar, to take into account the differences in the knee geometry during the force measuring process and the knee during normal operation.

Figure 8C:
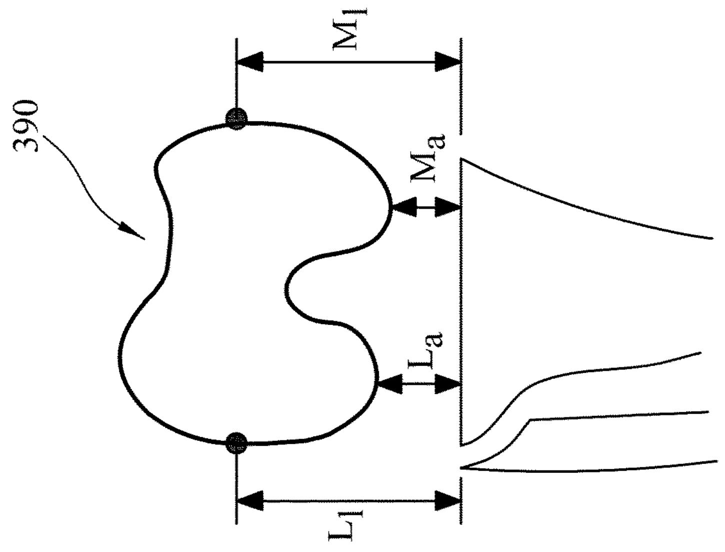
FIGS. 8A, 8B and 8C show respective views of a knee joint at a 90° flexion angle illustrating the distance between the condyles of a femoral implant and the tibial plane under a varus moment, a valgus moment and with the lateral and medial ligaments both in tension respectively.
Figure 8B:
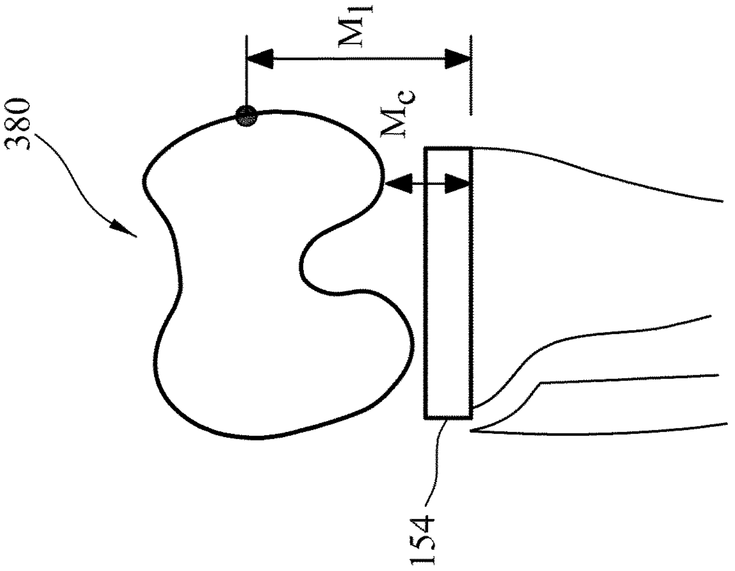
Figure 8A:
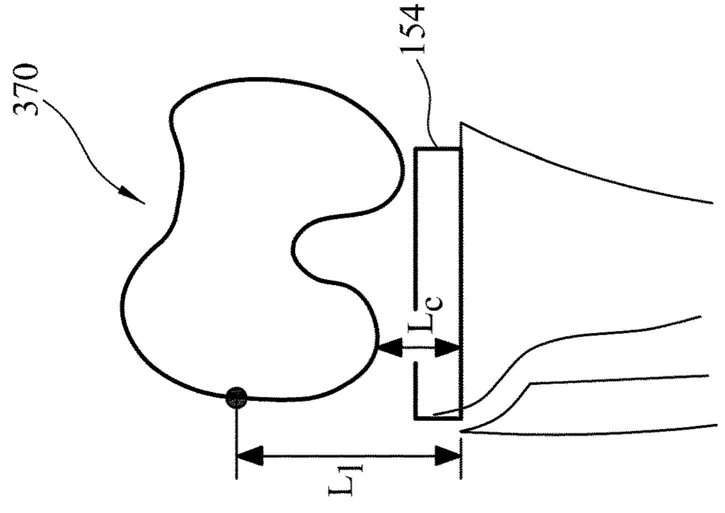

For example FIG. 8A shows a view of the knee 370 while a varus moment is applied during measurement of the force using the force sensor 154 and at a knee flexion angle of approximately 90°. As can be seen the distance between the resected tibial surface and the lateral native epicondyle of the femur is $L_l$ and the calculated distance between the resected tibial surface and the posterior part of the lateral native condyle of the femur is $L_c$.

Similarly, FIG. 8B shows a view of the knee 380 while a valgus moment is applied during measurement of the force using the force sensor 154 and at a knee flexion angle of approximately 90°. As can be seen the distance between the resected tibial surface and the medial native epicondyle of the femur is $M_l$ and the calculated distance between the resected tibial surface and the posterior part of the medial native condyle is $M_c$.

FIG. 8C shows a view of the knee 390 in which the soft tissues of the knee are taught and in the absence of the force sensor and at a knee flexion angle of approximately 90°. The actual distance between the resected tibial surface and the lateral native condyle is $L_a$ and the actual distance between the resected tibial surface and the medial native condyle is $M_a$. In practice $M_a > M_c$ and $L_a > L_c$. Hence, in order to establish more accurate values for the distances calculated previously, compensation factors may be used at 310 to correct the calculated values for the lateral $L_c$ and medial $M_c$ distances to correspond more closely to the lateral $L_a$ and medial $M_a$ distances when the soft tissue structures on both side of the knee are taught.

The compensation factors may be determined empirically. For example an anatomic study may be carried out to generate a database capturing the relationship between $L_a$ and $L_c$ and $M_a$ and $M_c$ at different knee flexions angle and that can be interpolated to provide correction factors for any particular values of $L_c$ and $M_c$. Another example would be to relate the correction factor to the epicondylar width, as the amount of correction increases with the width of the femur. For example a simple geometric formula or equation may be used to determine the correction factor to apply to correct $L_c$ to $L_a$ and $M_c$ to $M_a$ using the width femur and/or separation between the epicondyles of the femur.

Using a correction factor will improve the accuracy of the method but is not essential. As an example only, a typical value for the correction factor for an average adult knee may be about 20%. That is, La maybe approximately 20% greater than Lc, e.g., La is 120% of Lc.

Use of a correction factor in the range of about 10% to 30% can improve the accuracy but is not essential. Without the correction factor, the medial-lateral balance will still be correct, but the actual size estimates for the medial and lateral gaps will be undersized (by up to about 20%). This should be reasonably constant though and a consequence may be simply that a slightly thicker insert (20% thicker) than planned may be used in order to fill up the extra 20% of space in order to arrive at the target force.

Hence after step 310, the system has stored corrected values of the medial and lateral distance between the resected tibial surface and the femoral condyles for the planned femoral implant position for a target force $F_T$, and +/−5% values, over a range of knee flexion angles. This data may then be output, for example in a visual form, for the user and/or for use by other software processes.

Figure 9A:
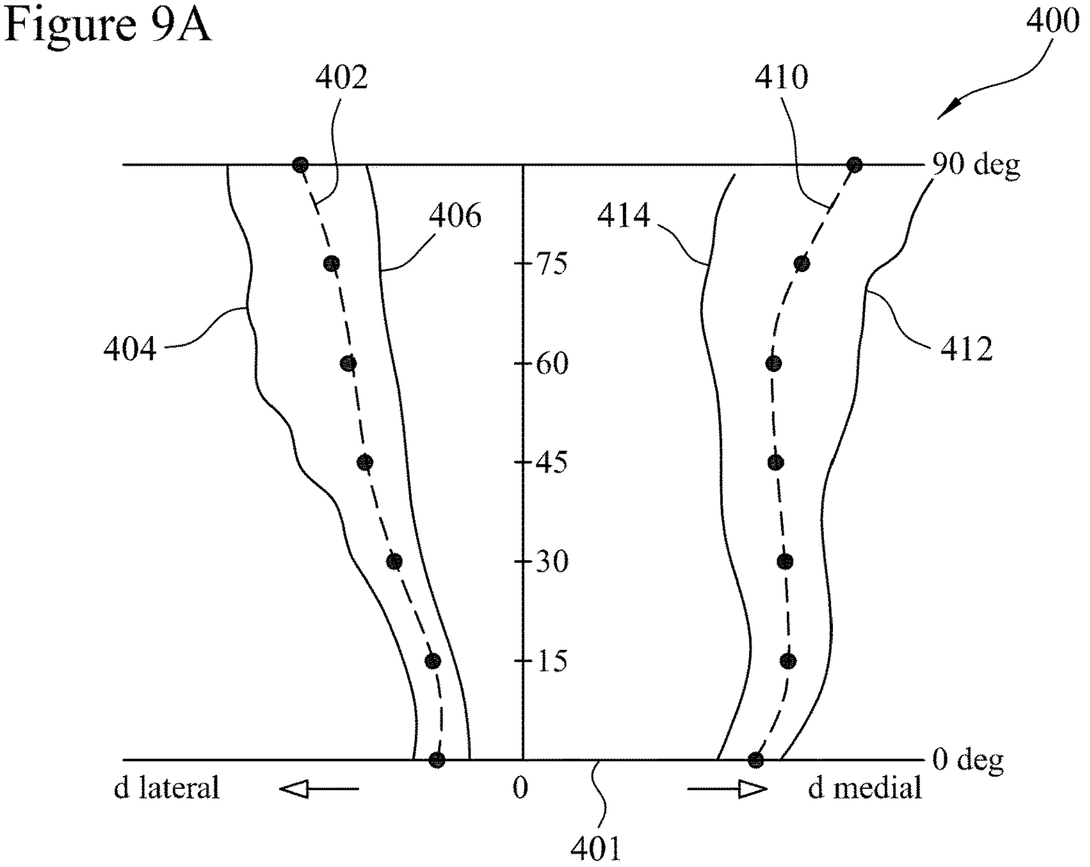
FIG. 9A shows a graphical representation of an output of the data processing method of FIG. 3 and illustrating the lateral and medial distance as a function of knee angle for a target lateral and medial force.

For example at 312, a graphical representation of the data may be output to the user as illustrated in FIG. 9A. FIG. 9A shows a graphical representation 400 of the variation in the lateral distance 402 and the medial distance 410 as a function of knee flexion angle (from 0° to 90°) for a set of target force values, $F_T$, and also $F_T$+5%, 404, 412, and also $F_T$−5%, 406, 414. The definition of the target force is the same for each knee angle, e.g. 110% of the cross over force, but the absolute value of $F_T$, will vary with knee flexion angle, and may also differ medially and laterally.

As can also be seen in the example illustrated by FIG. 9A, the lateral distance and the medial distance corresponding to the target force values is relatively smaller at full extension/no flexion and relatively larger at 90° flexion. Also, the amount and the way in which the medial and lateral distances vary in order to maintain the target forces differ. As will be appreciated the exact form of the graphs illustrated in FIG. 9A will vary from patient to patient depending on the specific soft tissue envelopes for each patient. The surgeon may use this data in order to assess and determine a suitable size for the medial and femoral distance, and hence any variation in the planned position for the tibial and/or femoral implants.

The plots 404, 406 and 412, 414 of sensitivity of the medial and lateral forces to medial and lateral distance also help the surgeon to understand that the sensitivity of the force in the ligaments to gap size is higher at lower flexion angles (0°) but lower at higher flexion angles (90°). Hence, setting the gap size on the lateral and medial sides at lower flexion angles may be preferable, for the specific example illustrated in FIG. 9A. However, this may not be the case for every knee and will depend on the specific shape of the graph for each patient.

In some embodiments, the process described above may be streamlined as follows.

Some structures, for instance medial or extension structures, may be relatively stiff. In such structures, the distraction forces described herein may have relatively little effect on the resulting distance measurement. An example of this is shown in FIG. 16, which shows a graph illustrating a measured force-distance characteristic of a knee joint at a particular knee flexion angle.

Figure 16:
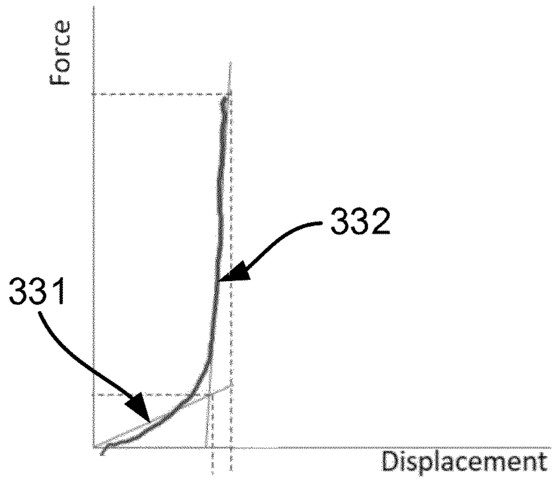
FIG. 16 shows a graph illustrating a measured force-distance characteristic of a knee joint at a particular knee angle.

In the example shown in FIG. 16, the generally linear first part 331, which is associated with ligament fibres aligning and/or straightening is similar to the generally linear first part 331 shown in, for example, FIG. 5. However, the second generally linear part 332, which is associated with ligament tissues stretching, is considerably steeper than that shown in FIG. 5. The steepness of the second generally linear part 332 in FIG. 16 is associated with a high degree of stiffness in the associated ligaments: within the second generally linear part 332, the change in distance associated with a given change in the applied force is relatively small.

The stiffness of the ligaments may be associated with a given range of knee flexion angles. For instance, the apparent stiffness of the ligaments may be higher within a certain range of knee flexion angles, but less pronounced at other knee flexion angles. Nevertheless, it is anticipated that stiff ligaments may generally lead to a relatively steep second generally linear part 332 across a range of knee flexion angles.

The stiffness of the ligaments would generally be evident to a surgeon taking the force/distance measurements described herein and would also be detected by the tracking system 102 of a CAS system 100 of the kind described herein.

For knee flexion angles at which the relatively high stiffness of the ligaments results in a steep second generally linear part 332, the process described herein in relation to FIG. 3 may be streamlined to some extent. In particular, for those knee flexion angles at which the medial and/or lateral collateral ligament response is stiff, the target distance may be set to a nominal value which is slightly less than the maximum gap (where the "maximum gap" is defined as the distance measurement taken at the maximum applied force during the force versus distance measurements described above in relation to FIG. 2). The choice as to whether to set the target distance in this way may be guided by predetermined parameters such as the amount of displacement observed across the range of forces applied within the second generally linear part 332 after the intermediate crossover region 333 (see FIG. 5) at that knee flexion angle. For instance, if the amount of displacement observed in the second generally linear part 332 (i.e. between the end of the intermediate crossover region 333 and the maximum force applied during the force versus distance measurements) is less than a certain threshold (e.g. 1 mm) then it may be determined that the ligaments at that knee flexion angle are sufficiently stiff that setting the target distance to the aforementioned nominal value is appropriate.

On the other hand, if the aforementioned threshold, which may also be referred to as a stiffness threshold, is not met or exceeded at any given knee flexion angle, then the normal methodology described herein in relation to FIG. 3 may be instead be followed, in which the target distance may be determined according to a target force $F_T$ and/or a range centred around $F_T$ such as $F_T$±5%.

It is envisaged that the approach described above, involving setting the target distance to the nominal value may be applied to lateral as well as medial force versus distance measurement results.

The use of the nominal value for the target distance for knee flexion angles having relatively steep second generally linear parts 332 may simplify the methodology shown in FIG. 3, since for those knee flexion angles, it may not be necessary to perform detailed calculations of distances at target forces based upon the data acquired in the method of FIG. 2. This may, for instance, allow steps 306 and 308 to be streamlined for those knee flexion angles corresponding to the medial and/or the lateral structures. Because the target distance (i.e. the chosen nominal value) is largely independent of the distraction force in the relatively steep second generally linear part 332, the lateral knee gap distance corresponding to the target force $F_T$ may be taken to be the nominal value itself. Similarly, because the target distance (i.e. the chosen nominal value) is largely independent of the distraction force in the relatively steep second generally linear part 332, the medial knee gap distance corresponding to the target force $F_T$ may be taken to be the nominal value itself.

It is envisaged that in some examples, this simplification may be applied to some or even all of the knee flexion angles (for the medial and/or lateral structures) involved in the overall procedure, namely any knee flexion angles in which the aforementioned stiffness threshold is met or exceeded.

It is noted setting the target distance to a nominal value that is slightly less (e.g. by an amount in the range 0.5 mm-1.0 mm) than the maximum gap can avoid over tensioning in the ligaments.

The tibial insert will result in a fixed medial and lateral distance between the tibial cut and the articulating surface of the currently planned femoral implant position though the range of flexion angles of the knee. For example, a particular thickness of tibial insert, providing the tibial articulating surface, may result in an actual medial and lateral distance, $M_a$ and $L_a$ of 10 mm. The medial and lateral forces likely to result from that distance may be calculated and output to the user.

The distance from the resected tibia to the femoral articulation surface is the thickness of the overall tibial component. Depending on the implant system that may be the thickness of a tibial tray and the thickness of the insert or in the case of an all polyethylene tibial component it is just the thickness of the polyethylene component. Also, some implant systems use a nomenclature where the insert thickness actually describes the thickness of the overall tibial construct (i.e. insert and tibial tray), whereas other implant system, use a nomenclature in which the insert thickness is the actual thickness of the insert alone. In that case the overall tibial construct has a thickness larger than this. So, for example, a tibial tray may have a thickness of 4 mm, in which case, for an insert thickness of 5 mm, the overall thickness of the tibial construct, would be 9 mm.

In the following description, the value of 6 mm represents a 6 mm thick insert, and so the actual thickness of the overall tibial construct (insert +4 mm tibial tray) and hence the distance between the resected tibia and femoral articulation surface, $L_a/M_a$, is 10 mm.

So, in some instances, for convenience for the surgeon, the distance between the resected tibia and femoral articulation surface, $L_a/M_a$, may be calculated, but may be plotted as a distance that takes into account a fixed tray thickness, e.g. 4 mm, so that the numbers correspond to the number that the surgeon is interested in for the implant system being used, e.g. the insert thickness to use.

As illustrated in FIG. 3, at 314 a selected tibial insert thickness, e.g. 6 mm, may be entered and the resulting lateral and medial distance, e.g. 10 mm, for the currently planned implant positions may be calculated. Then at 316, the medial and lateral forces arising from that lateral and medial distance at different knee flexion angles may be calculated from the force-distance characteristics (see e.g. FIGS. 5, 6 and 7). Then at 318, the calculated values for the medial and lateral forces as a function of knee flexion angle may be output to the user.

Figure 9B:
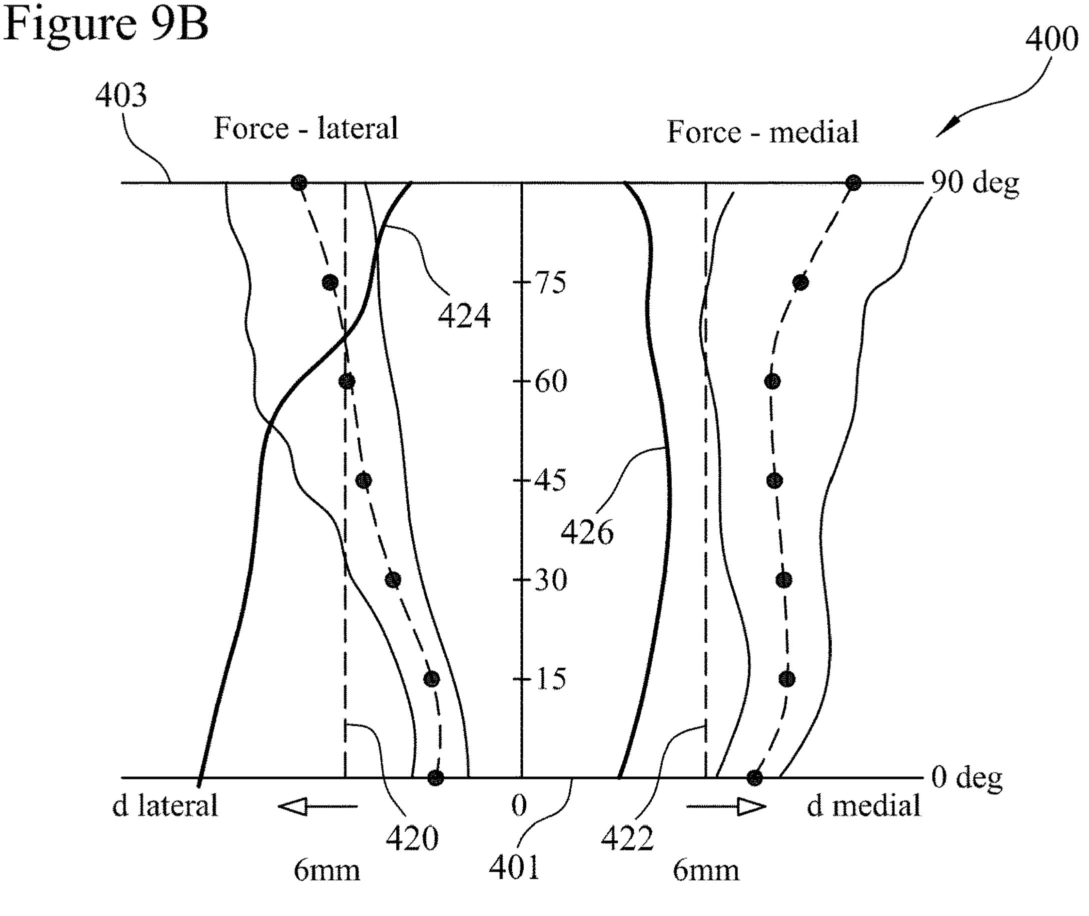
FIG. 9B shows the graphical representation of FIG. 9A with a predicted lateral and medial force as a function of knee angle for a particular planned knee gap distance.

For example, FIG. 9B shows a plot of the variation of the lateral force 424 and the medial force 426 with knee flexion angle overlaid on the graphical output 400 illustrated in FIG. 9A. In the described example, the entered insert thickness of 6 mm corresponds to a constant medial distance 420 and a constant lateral distance 422 of 10 mm on the scale of the lower distance axis or abscissa 401. Line 424 corresponds to the calculated lateral force as a function of knee flexion angle and line 426 corresponds to the calculated medial force as a function of knee flexion angle on the scale of the upper force axis or abscissa 403. Hence, the user can see what effect the planned inert thickness of 6 mm and implant positions will likely have on the lateral force 424 and medial force 426 in the knee.

As illustrated in FIG. 9B, the current plan is predicted to give rise to a reasonably constant medial force but a quite widely varying lateral force. As illustrated in FIG. 9B the native lateral gap 402 is less than 6 mm (as illustrated by line 420) in extension and so would give rise to a large lateral force (as illustrated by line 424) in extension, and that the amount of the lateral force would reduce in flexion as the native gap is closer to 6 mm. the medial force (illustrated by line 426) is relatively constant with knee angle, and relatively low, as 6 mm (illustrated by line 422) is less than the native gap and the difference between the native gap and 6 mm is relatively constant.

At 320, the user may determine whether current plan is acceptable or not and if not then at 322 the user may modify the plan. As illustrated in FIG. 3, if the modification is only to the insert thickness, the processing may simply return 324 to step 314 and modified medial and lateral force values may be calculated for the new medial and lateral distances.

Additionally or alternatively at 322, the user may modify the planned position of the femoral component in particular. Some modification of the tibial component plan may be possible at this stage even though the tibia has already been resected. For example recuts are possible and relatively easy to achieve particularly in embodiments using surgical robot 106. Hence, recuts may be made, for example to make changes to the angle of the resected tibia. When bone is removed a larger insert may be used to compensate for the removed bone so as to achieve a better balanced joint.

For example, in the specific situation illustrated in FIG. 9B, the surgeon could change the angle of the distal femoral resection to remove more lateral bone and remove less medial bone which would help to correct the extension gaps on the graph. Then, in flexion, the femoral rotation could be changed to take a similar amount of bone off the lateral side, but less bone off the medial side, to decrease the resulting gap medially.

As the tibial insert results in a constant distance throughout the flexion range, it is desirable to have a planned femoral implant position that results in a medial and lateral distances corresponding to the target forces, that are reasonably constant throughout much of the range of knee flexion and which also have similar medial and lateral values. Therefore, at step 322, the user may modify the planned position of the femoral component as described above. As the position of the femoral component is defied relative to the anatomy of the femur and the position of that is known as the tracked femoral marker or array 150 is attached to the femur 142, the planned position of the femoral implant may also be determined relative to the position of the tracked femoral marker. Hence, processing returns 326 and a modified femoral plan may be used and steps 304 onward may be repeated using the modified planned position of the femoral implant and hence giving rise to different initial force-implant gap functions for each knee angle. There is no need to repeat the measurement of the force data as the physical native femur has not changed, simply the planned position of the femoral implant relative to the native femur.

Figure 10A:
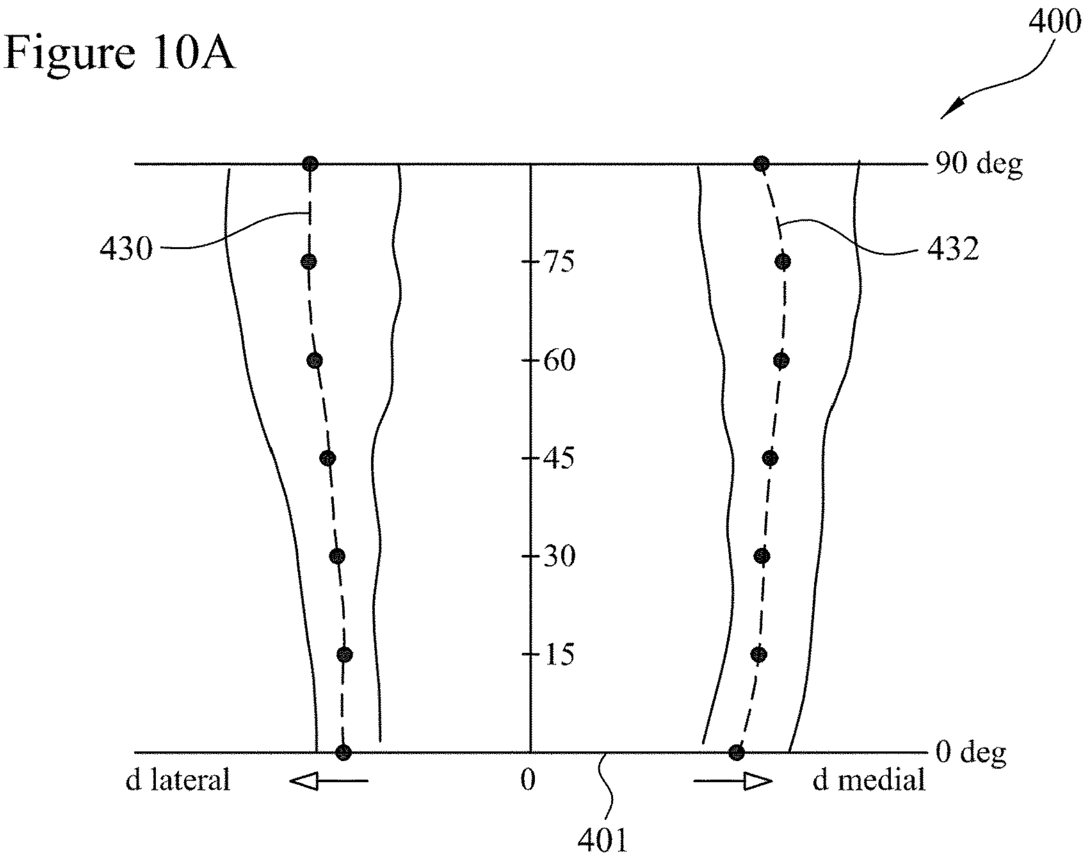
FIG. 10A shows a graphical representation of an output of the data processing method of FIG. 3 and illustrating the lateral and medial distance as a function of knee angle for a target lateral and medial force for a modified implant plan.
Figure 10B:
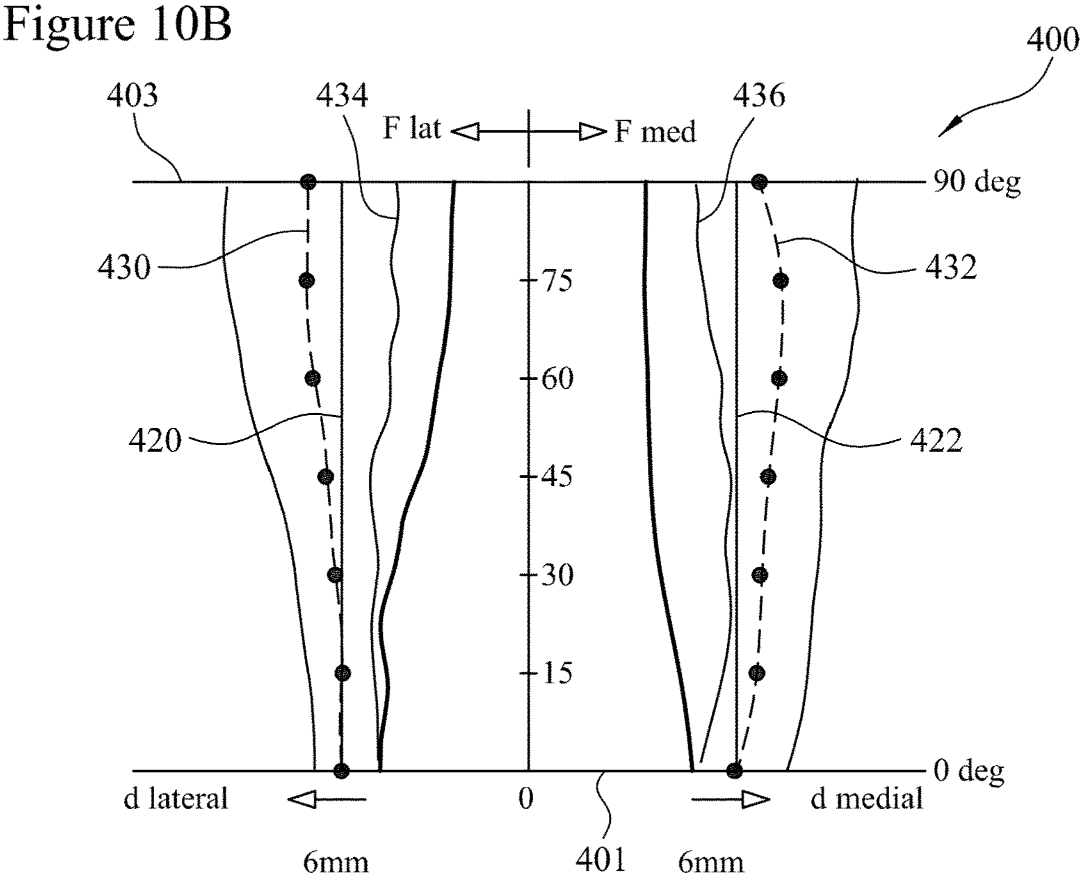
FIG. 10B shows the graphical representation of FIG. 10A with a predicted lateral and medial force as a function of knee angle for the modified planned knee gap distance.

FIGS. 10A and 10B illustrate the graphs output by the method at steps 312 and 318 respectively for such a modification of the surgical plane. As illustrated in FIG. 10A, the modified planned implant positions give rise to a more constant lateral distance 430 for the target lateral forces as a function of knee angle and a more constant medial distance 432 for the target medial forces as a function of knee angle compared to FIG. 9A. As illustrated in FIG. 10B, The resultant graph output at 318, has a predicted lateral force plot 434 and a predicted medial force plot 436 which are closer to constant, but not perfectly constant, as a function of knee angle, and resulting in a knee possibly slightly more lax in flexion. As also illustrated in FIG. 10B, the lateral knee gap 430 and medial knee gap 432 for the modified implant plan are respectively closer to the planned implant thickness of 6 mm, as illustrated by lines 420 and 422.

Hence, steps 304 onward of the method 300 may be repeated one or more times until the user is happy with the planned femoral position and resulting knee gap distance for a selected tibial insert thickness.

Figure 11:
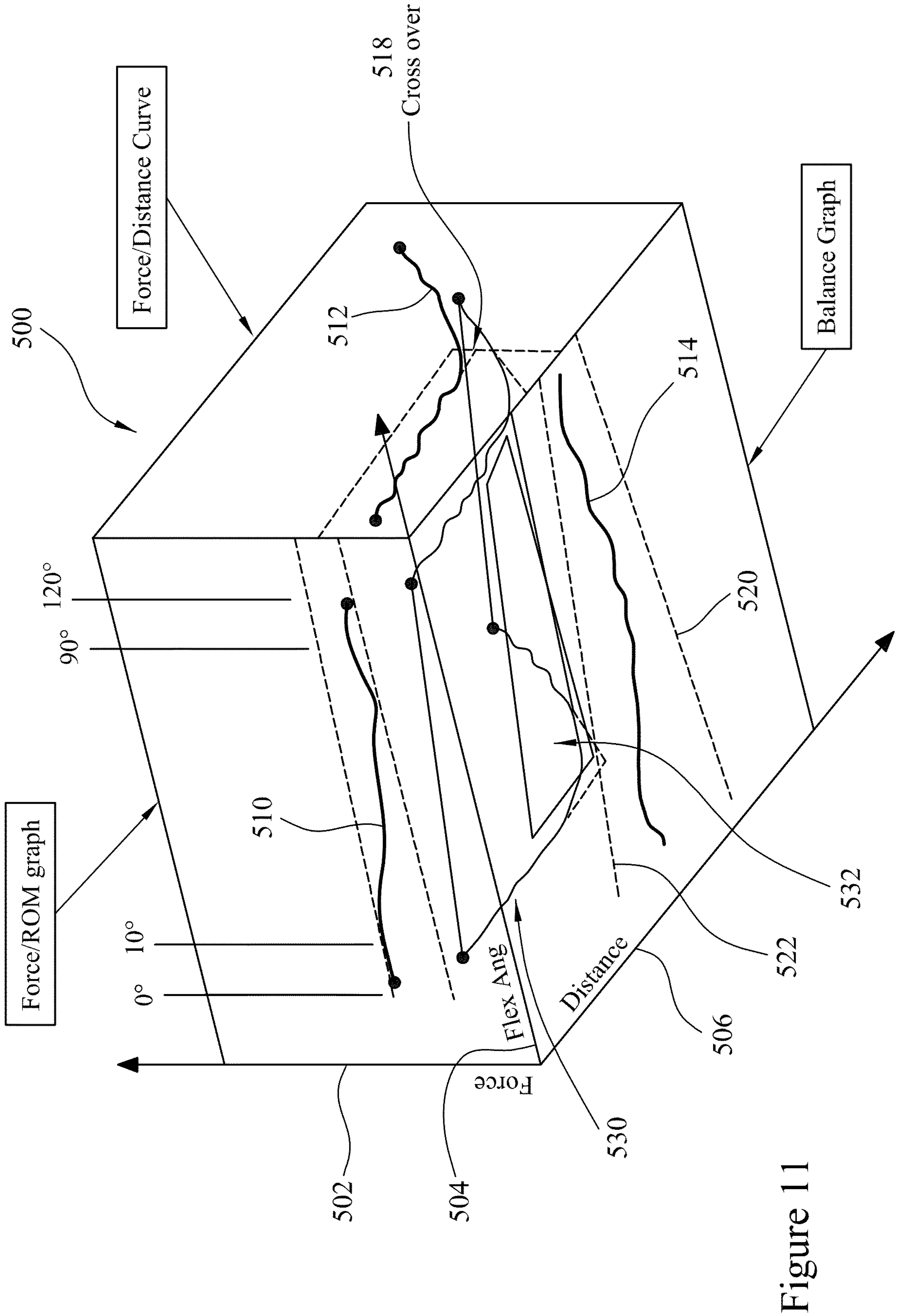
FIG. 11 shows a further graphical representation an output of the data processing method of FIG. 3 and illustrating the variation of various properties as a function of one or more of force, knee flexion angle and knee distance for either the lateral or medial part of the knee joint.

FIG. 11 shows a further visualisation 500 of the data stored by the system and that may be output to the user at steps 312 and/or 318 additionally or alternatively to the data visualisations illustrated in FIGS. 9A, 9B, 10A and 10B. The data visualisation 500 illustrated in FIG. 11 includes an axis for measured force 502, an axis for knee flexion angle 504 and an axis for knee distance or gap. As will be appreciated FIG. 11 illustrates a data visualisation for only a single side of the knee, and so in practice two instances of data visualisation 500 may be output to the user at the same time, one for the medial side and one for the lateral side of the patient's knee.

Hence, plot 510 corresponds to measured force as a function of knee flexion angle (for a particular knee distance) plot 512 corresponds to a measured force-distance characteristic (for a particular knee flexion angle) and hence is similar to FIGS. 5, 6 and 7, and plot 514 corresponds to a knee distance or gap corresponding to the cross over force value 518 as a function of knee flexion angle, and hence similar to plots 402 and 410 of FIG. 9A. Also shown are the variations 520 and 522 in knee gap corresponding to the target force plus or minus 5%. Plot 530 is a surface illustrating how the measured force-distance characteristic varies as a function of knee flexion angle. And plot 532 corresponds to a region of surface 530 bounded by the target force plus and minus 5% and hence representing the range of knee gap values corresponding to the target forces plus and minus 5% as a function of knee flexion angle. Some or all of data illustrated in FIG. 11, and various different combinations of the data illustrated in FIG. 11, may be output to the user at various stages of the method illustrated in FIG. 3 for each of the medial and lateral sides of the knee joint, and changes to the data arising from different insert thicknesses and/or changes to the planned implant positions as discussed above and/or otherwise.

The surgical procedure may then continue in a generally conventional manner and using the panned femoral implant position and tibial insert thickness arrived at after step 320. Hence, once the surgeon is happy with the planned implant positions at 226 of FIG. 2, the remainder of the knee replacement surgical procedure may proceed generally as conventionally.

A second embodiment will now be described which is similar to the first embodiment in many respects and differs largely in that the minimal perpendicular distance between the tibia and the lateral native femoral epicondyle and the medial native femoral epicondyle are used instead of the medial and lateral condyles. This can avoid using compensation factors as described above and illustrated in FIGS. 8A to 8C in connection with the first embodiment.

Hence many of the steps of method 200 and process 300 are either generally the same or need only minor modification, as will be apparent to a person of ordinary skill in the art, form the further description herein. Indeed, method 200 is substantially the same in terms of how the force data and data from the tracking markers 150, 152 is generated and stored by the CAS system.

Figure 12:
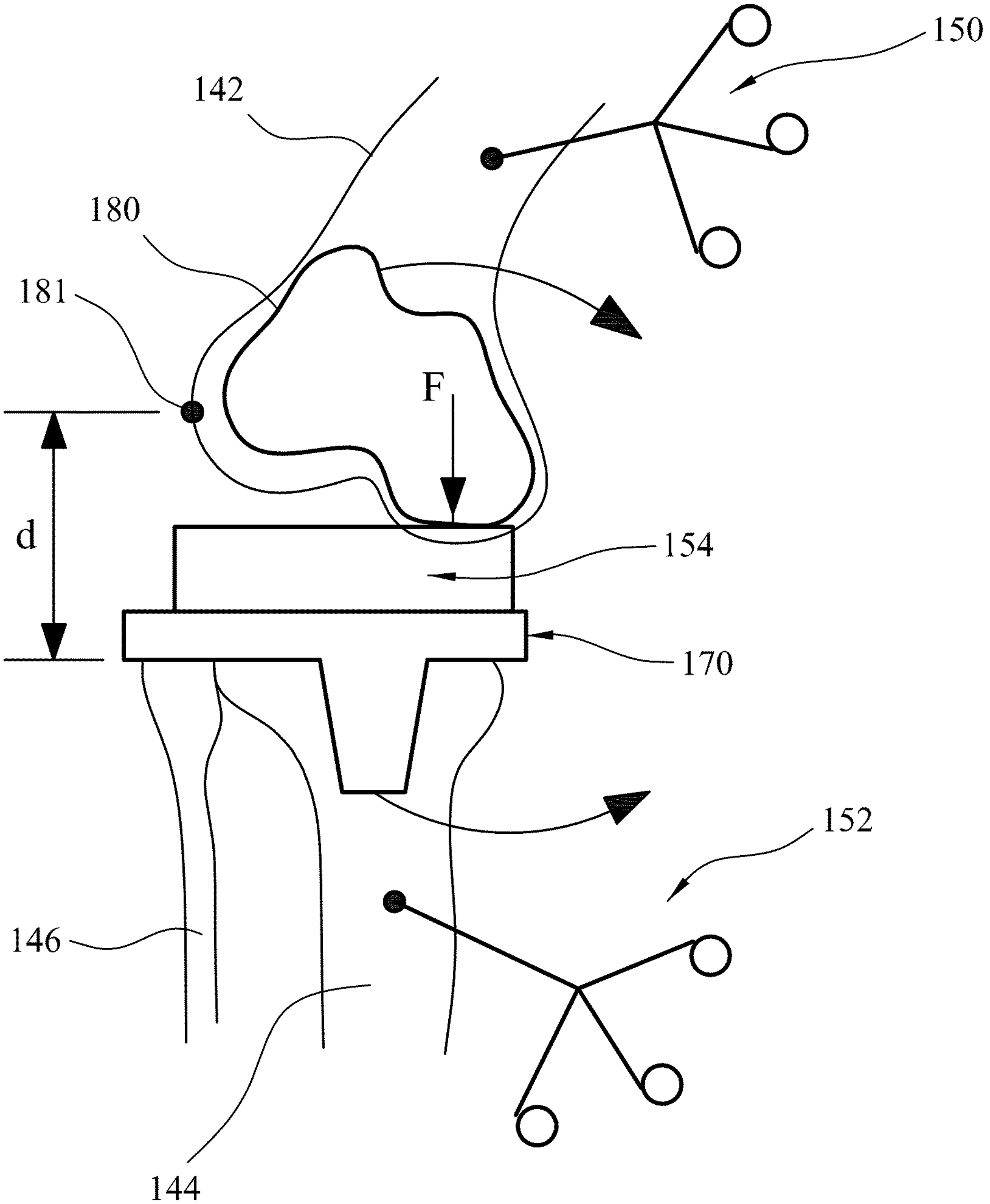
FIG. 12 shows a further illustration of a knee joint under a varus load and including the planned positions of femoral and tibial implants illustrating a second distance that may be used in a further embodiment of the data processing method.

However, at step 304, the distance calculated for the force-implant distance function is the minimal perpendicular distance from either the resected surface of the tibia, or the planned tibial resection surface, and the lateral epicondyle of the planned femoral implant position or the medial epicondyle of the planned femoral implant position, as illustrated in FIG. 12. FIG. 12 shows the force sensor 154 mounted on the native tibia, the planned position of the tibial implant 170, the planned position of the femoral implant 180 and the minimal perpendicular distance, d, from the planned resected surface of the tibia 171 and the lateral epicondyle 181 of the native femur. The native femur epicondyle is generally the point where the collateral ligaments attach and hence is a useful anatomical landmark in assessing changes in tension in the ligaments.

Again, if the actual tibial cut has been made and registered then the minimal perpendicular distance from the actual tibial cut to each of the medial and lateral epicondyles may be calculated and used instead. Also, if a film sensor on the native surface of the tibia is used then there is no need to make the tibial cut during method 200 and then the minimal perpendicular distance from the native tibia to each of the medial and lateral epicondyles may be calculated and used instead. Alternatively, it may be more computationally convenient to use the planned tibial cut position, if the tibial cut has not been made, so that a flat plane is used rather than the more complex 3D surface of then native tibia. Hence, below, the tibial plane will generally be used to mean the actual plane of the resected tibia or the plane of the planned tibial resection. Hence, even if a film force sensor is used on the native tibia, then the calculations may be based on the planned position of the tibial cut. A benefit of this is that more options are retained for changing the tibial cut, as the tibia has not yet been cut and therefore the compromises associated with a recut may be avoided.

Processing then proceeds at steps 306 and 308 in which the medial and lateral force-distance functions for each knee flexion angle determined at 304 are used to determined medial and lateral distances corresponding to medial and lateral target force values and target force values +/−5% over the range of knee flexion angles.

Figure 13:
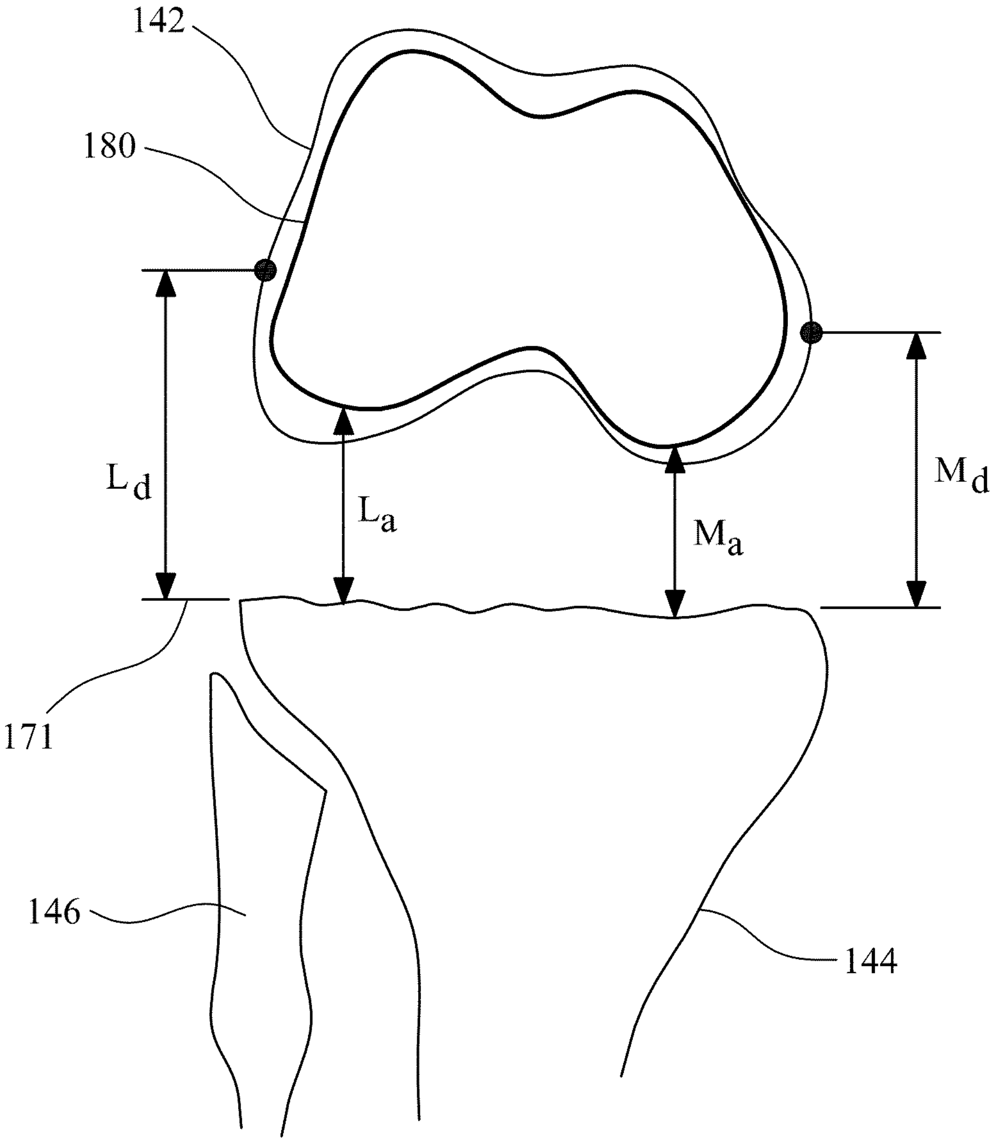
FIG. 13 shows a view of the knee joint of FIG. 12 at a 90° flexion angle illustrating the relationship between an epicondylar distance and a corresponding knee joint gap distance with the lateral and medial ligaments both in tension.

Then, instead of the compensation step 310, a femoral position modelling step is carried out. In particular, the position of the native femur having the previously calculated medial and lateral distances corresponding to the target force values for each knee flexion angle is determined. For example, FIG. 13, shows the modelled position of the native femur 142 relative to the tibia at a knee flexion angle of approximately 90° and having the lateral distance Ld and medial distance Md corresponding to the target force at the 90° knee flexion angle. For the native femur position so determined, the minimum perpendicular distance from the tibial cut (either actual or planned) to the planned position of the lateral condyle, La, and to the planned position of the medial condyle, Ma, for the initial planned position of the femoral implant 180 are calculated. The calculation of the minimum perpendicular distance from the tibial cut (actual or planned) and the planned position of the lateral condyle and medial condyle is carried out for each knee flexion angle. The procedure is then repeated for the medial and lateral distances corresponding to the target force +5% and the target force −5%.

The method then resumes as illustrated in FIG. 3 at step 312 in which the medial and lateral distance as a function of knee flexion angle for the target force value and +/−5% can be output and displayed to the user, similarly to FIG. 9A. Again the thickness of the tibial insert can be entered and a resulting lateral and medial force can be calculated at 316 and output at 318 by using the force-distance characteristics and modelling the position of the femur and resulting position of lateral and medial condyles of the planned position of the femoral implant for each knee flexion angle.

Again, based on the output data the user can determine whether the planned tibial insert thickness and/or planned femoral implant position is acceptable or not at 320 and the insert thickness may be changed and/or the planned femoral implant position. However, in this second embodiment, there is no need to repeat the modelling of the femur position at different knee flexion angles. All that needs to be done is to re-calculate the perpendicular lateral distance, La, and medial distance, Ma, from the tibial cut to the modified position of the lateral condyle and medial condyle of the femoral implant at its new position relative to the native femur. The positional relationships between the tibial and femoral tracking markers, the femoral epicondyles and the forces are already known.

Figure 14:
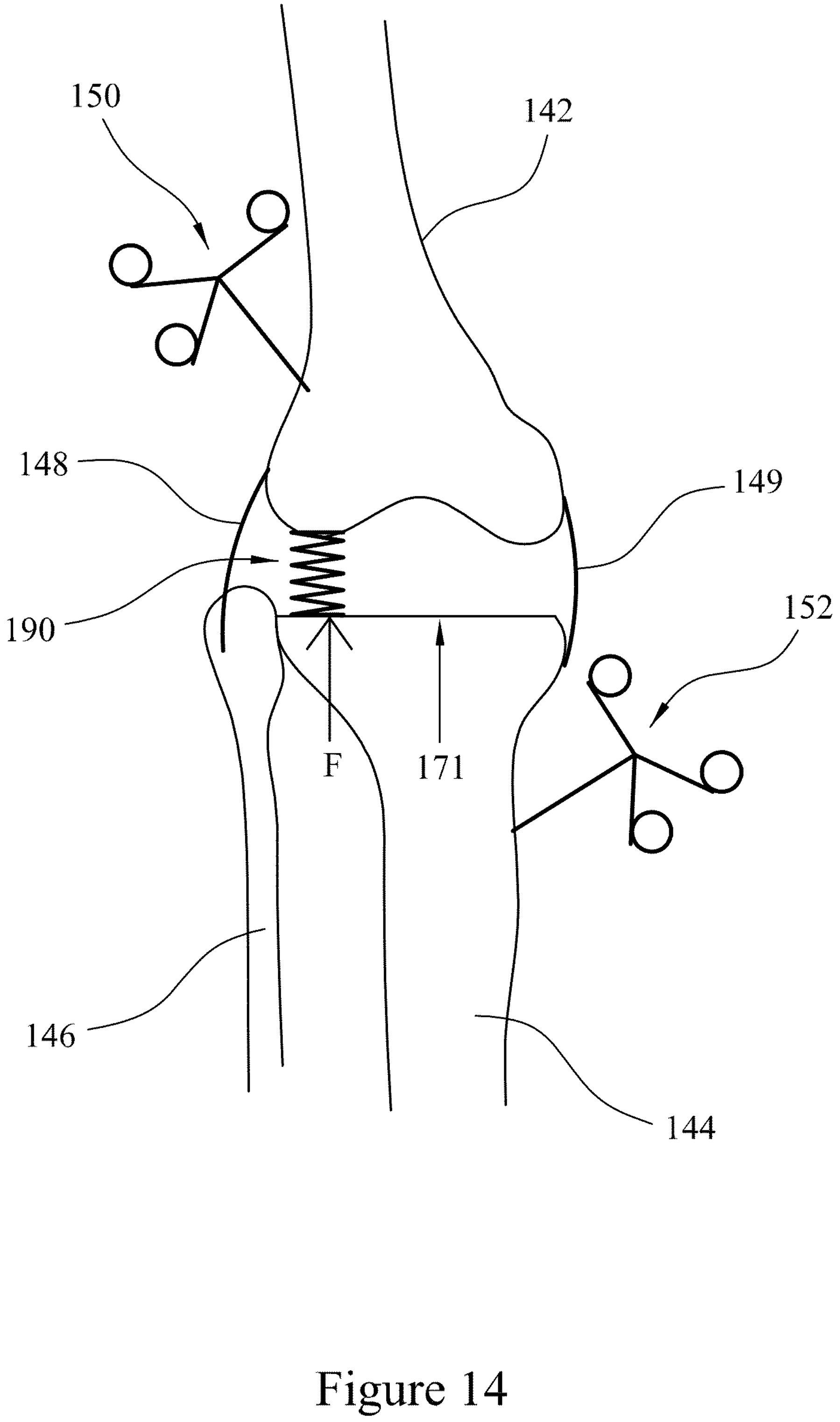
FIG. 14 shows a schematic anterior view of a patient's knee including a tensionmeter.

FIG. 14 shows an alternative approach to that illustrated in FIG. 1. Instead of using an electronic force sensor to measure the forces, instead, a tension meter may be used. As illustrated in FIG. 14, a tension meter 190 may be inserted into the knee space between the resected tibia plateau 171 and a femoral condyle. As illustrated in FIG. 14, the tension meter is located adjacent the lateral collateral ligament 148 and the lateral condyle of the femur 142.

Figure 15:
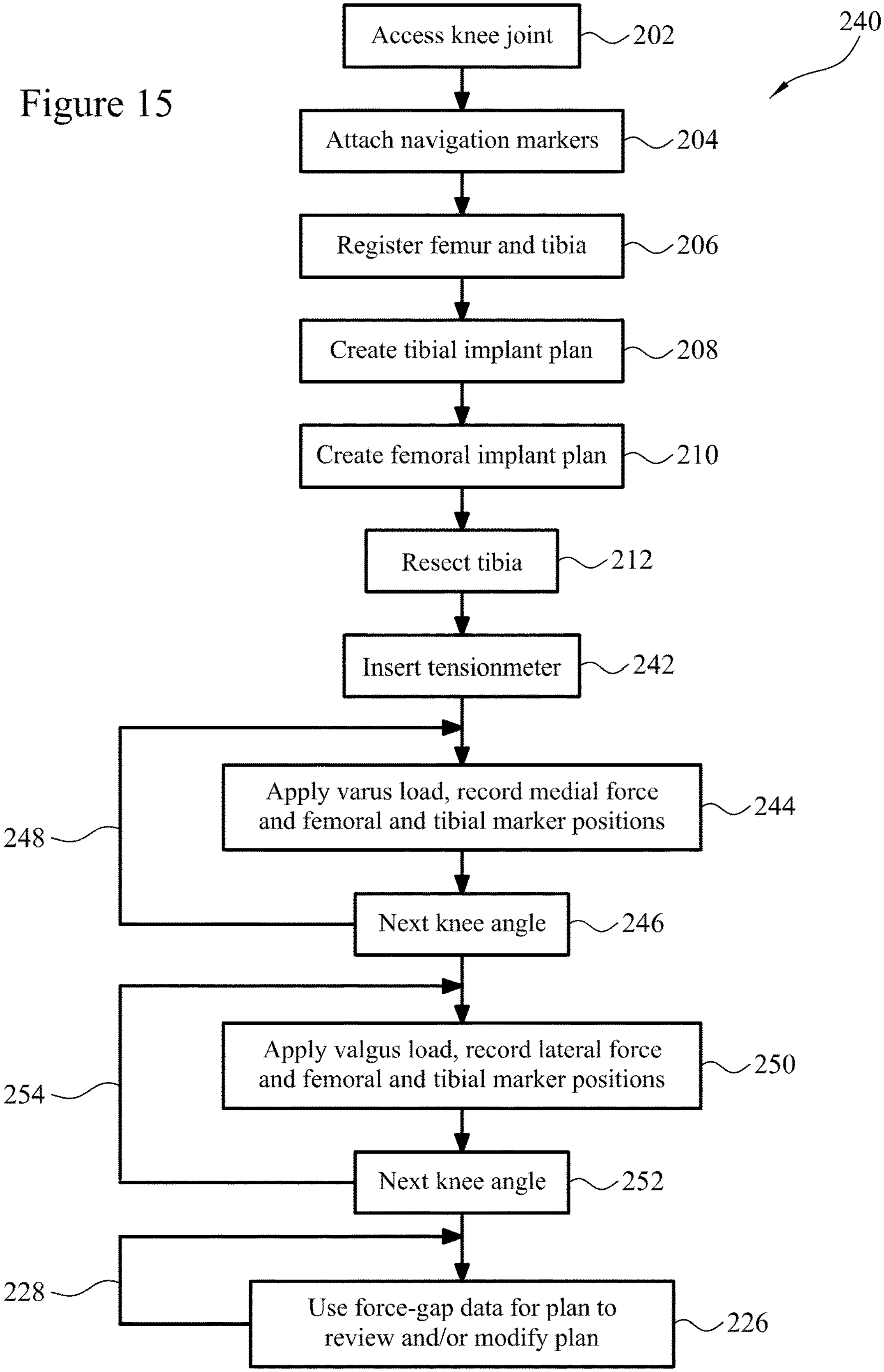
FIG. 15 shows a flow chart illustrating a method according to a further embodiment.

FIG. 15 shows a flowchart illustrating the surgical procedure used to capture the force-displacement data using the tension meter 170 illustrated in FIG. 14. The method 240 illustrated in Figure is generally similar to method 200 illustrated in FIG. 2. Only significant differences will therefore be described below.

Again, initially the knee joint is accessed at 202 and navigation markers attached to the tibia and femur at 204. At 206, the native femur and the native tibial are registered using the trackable pointer 156. At 208 and 210 the femoral plan and the tibial plan are created and at 212 the tibia is resected using the planned tibial cut, for example using a navigated tibial cutting block. Then at 242, the tension meter 190 is inserted in the knee gap between the resected tibial plateau and a one of the lateral or medial condyles. For example, as illustrated in FIG. 13, at 244, the tensionmeter 190 is used to apply an increasing load to the medial condyle. The positions of the femoral marker 150 and the tibial marker 152 are captured and the force applied to the medial condyle is read from the tension meter and entered into the data processing system. This may be done manually or electronically if an electronic tension meter is used. At 246, the knee is placed in a next knee angle and the procedure is repeated as illustrated by flowline 248 and the tension meter is used again to apply increasing loads to the medial condyle and the corresponding positions of the femoral marker 150 and tibial marker 152 are recorded at a variety of increasing load levels.

Once the medial measurements have been carried out, then at 250, the tension meter is moved to the lateral side and again used to apply an increasing load to the lateral condyle to tension the lateral ligament and the femoral marker and tibial marker positions are tracked and measured for a current knee flexion angle. Again, at 252 the knee is placed in a new knee flexion angle and the measurements repeated as illustrated by line 254.

Alternatively, a medial value and a lateral value could be measured at each angle, rather than doing all medial measurements and then all lateral measurements.

At 226, the force-distance data generated by data processing system 104 may be used by the surgeon to assess and/or review and/or modify the planned implant positions as illustrated by process flow line 228.

The data processing operations carried out by the data processing system are substantially the same as those described previously, but the manner in which the force-distance data is collected as a function of knee flexion angle is different.

FIGS. 17A to 17E show various steps for obtaining a measured force-distance characteristic of a knee joint at a particular knee angle, using a pivoting tensioner.

A number of devices such as distractors or pivoting tensioners are known in the art, which may be used in the approach shown in FIGS. 17A to 17E. Examples of automated/electronic sensor distractors which may be used are disclosed in U.S. Pat. Nos. 8,197,489 and 7,615,055, which are incorporated herein by reference in their entirety. An example of a manual distractor (known as a Themis distractor) which may be used is disclosed in U.S. Pat. App. Pub. No. 2020/0305943, which is incorporated herein by reference in their entirety.

Figure 17A:
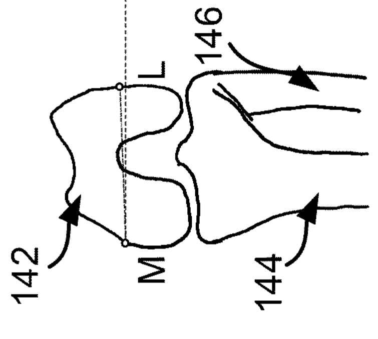
FIGS. 17A to 17E show various steps for obtaining a measured force-distance characteristic of a knee joint at a particular knee angle, using a pivoting tensioner.

FIG. 17A shows a knee joint upon which the measured force-distance characteristic is to be obtained. The knee joint is the knee joint of the left leg of the patient, in this example. The joint femur 142, tibia 144 and fibula 146 can be seen in FIG. 17A, and the medial and lateral sides of the joint are marked by "M" and "L", respectively. The patella is omitted for the sake of clarity.

Figure 17B:
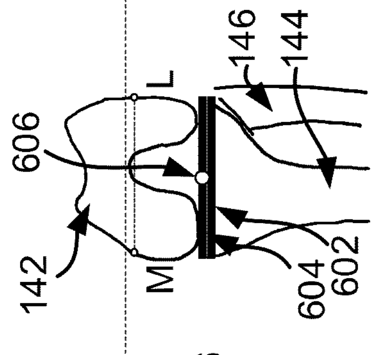

In a first stage, shown in FIG. 17B, tibial resection is made, and a pivoting tensioner is inserted into the joint. The pivoting tensioner includes an inferior plate 602 and a superior plate 604. The inferior plate 602 rests upon the resected surface of the tibia 144. The superior plate 604 engages with the femur 142. The inferior plate 602 and the superior plate 604 are coupled together in a manner that allows the superior plate 604 to be moved apart from the inferior plate 602 and to be pivoted about a pivot point 606. The pivoting movement of the superior plate 604 can allow the medial and lateral distraction of the joint, applied by the pivoting tensioner to be adjusted separately. Initially, as shown in FIG. 17B, the pivoting tensioner is in a collapsed configuration, in which the superior plate 604 is not spaced or pivoted with respect to the inferior plate 602. In this configuration, both the medial and lateral collateral ligaments are lax.

Figure 17C:
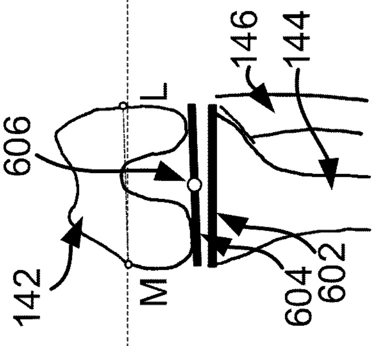

In a next stage, shown in FIG. 17C, the superior plate 604 is moved away from the inferior plate 602, to distract the femur 142 away from the tibia 144. This causes the medial and lateral collateral ligaments to lose their laxness and become tight. In this stage the movement of the superior plate 604 is substantially vertical, and the superior plate 604 is not tilted.

Figure 17D:
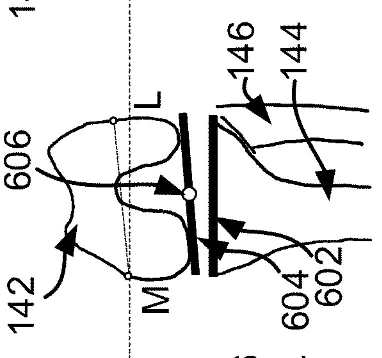

In a next stage, shown in FIG. 17D, the superior plate 604 moved further away from the inferior plate 602, which increases the distraction force acting between the femur 142 and the tibia 144. In this stage, the superior plate 604 begins to tilt such that the lateral gap is larger than the medial gap. There is little or no movement of the medial epicondyle in this stage, owing to the stiffness of the medial collateral ligament in this example. On the other hand, the increased lateral epicondyle continues to move in this stage, as the lateral collateral ligament stretches. Thus, in this stage, the femur 142 rotates around the medial epicondyle.

Figure 17E:
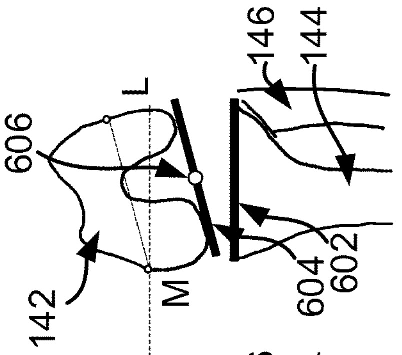

In a next stage, shown in FIG. 17E, the superior plate 604 moved again further away from the inferior plate 602, which again increases the distraction force acting between the femur 142 and the tibia 144. As with FIG. 17D, the superior plate 604 tilts such that the lateral gap becomes larger than the medial gap, and there is little or no movement of the medial epicondyle in this stage, owing to the stiffness of the medial collateral ligament in this example. Thus, in this stage, the femur 142 continues to rotate around the medial epicondyle. During this stage however, the lateral epicondyle reaches its position of maximum distraction, associated with the maximum tightness of the lateral collateral ligament.

As will be described below, the pivoting tensioner may include electrical/mechanical sensors or other means of determining the forces operating between the superior plate 604 and the inferior plate 602. This may include one or more pressure sensors which are configured to electrically output force values, and/or a mechanical indicator, which may be visually read off by the surgeon.

Figure 18A:
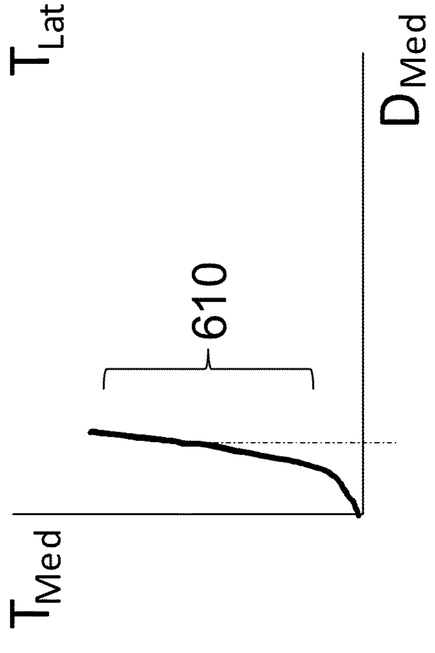
FIGS. 18A and 18B show graphs illustrating an example of the measured force-distance characteristics of a knee joint at a particular knee angle, using the approach shown in FIGS. 17A-17E.
Figure 18B:
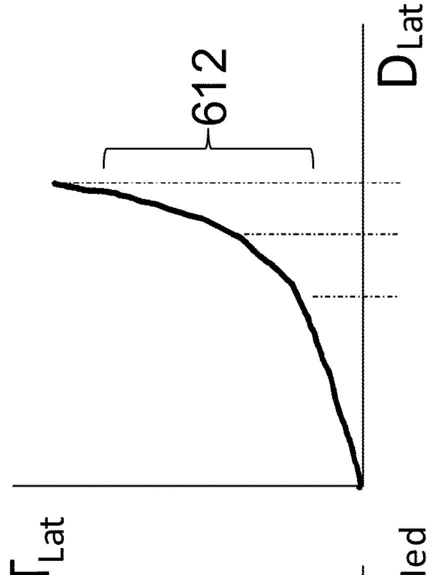

FIGS. 18A and 18B show graphs illustrating an example of the measured force-distance characteristics of a knee joint at a particular knee angle, using the approach shown in FIGS. 17A-17E. As described in relation to FIGS. 17A-17E, in that example the medial collateral ligament is rather stiffer than the lateral collateral ligament, whereby the femur 142 tends to rotate around the medial epicondyle. This is reflected in the measured force-distance characteristics shown in FIGS. 18A and 18B. Note that the second linear portion of the medial force-distance characteristic 610 shown in FIG. 18A is relatively steep, in comparison to the second linear portion of the lateral force-distance 612 characteristic shown in FIG. 18B.

Figure 19A:
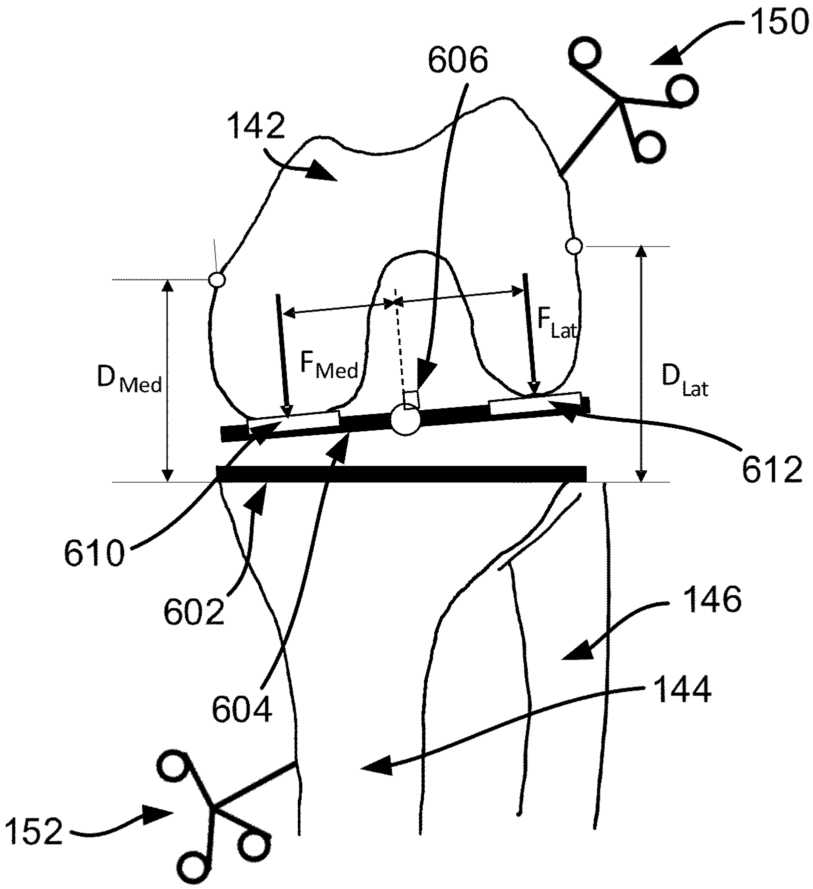
FIG. 19A shows further details regarding the approach taken in FIGS. 17A to 17E for obtaining a measured force-distance characteristic of a knee joint at a particular knee angle, using a pivoting tensioner.

FIG. 19A shows further details regarding the approach taken in FIGS. 17A to 17E for obtaining a measured force-distance characteristic of a knee joint at a particular knee angle, using a pivoting tensioner. In particular, FIG. 19A shows a pivoting tensioner including a medial force sensor 610 and a lateral force sensor 612. In the example of FIG. 19A, a first reference array 150 and a second reference array 152 of the kind described above are also provided, so as to allow a tracking system 102 of a CAS system 100 of the kind described herein to track the epicondylar distances to the tibial cut.

Figure 19B:
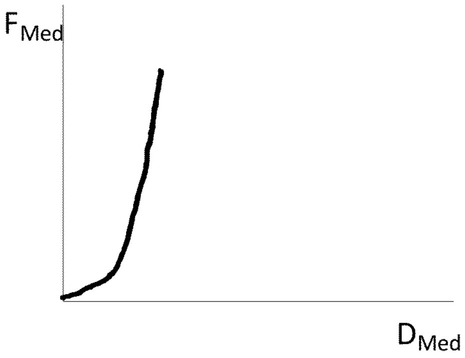
FIGS. 19B and 19C show graphs illustrating an example of the measured force-distance characteristics of a knee joint at a particular knee angle, using the approach shown in FIG. 19A.
Figure 19C:
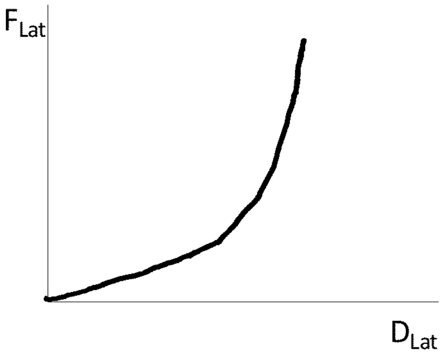

The use of the force sensors 610, 612 in combination with the reference arrays 150, 152 allow force and distance data to be collected in a synchronised manner, while the superior plate 604 is moved in the manner described above in relation to FIGS. 17A-17E. Moreover, this approach may allow the medial and lateral force-distance characteristics (see FIGS. 19B and 19C, respectively) of a knee joint for a given knee flexion angle to be collected simultaneously.

Figure 20A:
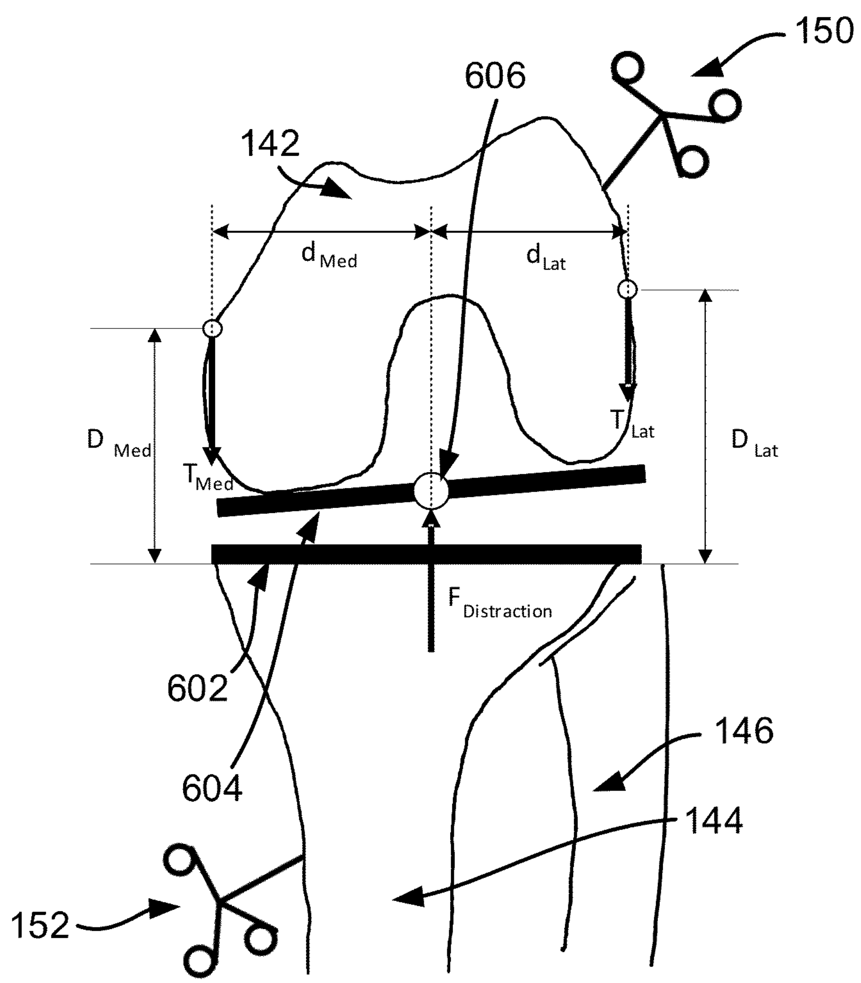
FIG. 20A shows further details regarding the approach taken in FIGS. 17A to 17E for obtaining a measured force-distance characteristic of a knee joint at a particular knee angle, using a pivoting tensioner; and x.

FIG. 20A shows further details regarding the approach taken in FIGS. 17A to 17E for obtaining a measured force-distance characteristic of a knee joint at a particular knee angle, using a pivoting tensioner. In the example of FIG. 19A, the pivoting tensioner includes separate medial and lateral force sensors 610, 612. However, as is illustrated by FIG. 20A, if the central distraction force $F_{Distraction}$ is known (along a direction parallel to a surface normal of the inferior plate 602), then calculations may be applied to resolve the forces and moments involved, for determining the tension in the medial ($T_{Med}$) and lateral ($T_{Lat}$) collateral ligaments. The central distraction force $F_{Distraction}$ may be determined by a single electrical sensor provided in the pivoting tensioner and/or may be read off by the surgeon, as described above.

As described in relation to FIG. 19A, a first reference array 150 and a second reference array 152 of the kind described above may also be provided, so as to allow a tracking system 102 of a CAS system 100 of the kind described herein to track the epicondylar displacements as the superior plate 604 is moved. To allow calculations for resolving the forces and moments involved to be performed, the location of the hinge point 606 of the pivoting tensioner (as well as the attachment points of the medial and lateral collateral ligaments) may also be registered and tracked by the tracking system 102. In particular, this can allow the distances $d_{Med}$ and $d_{Lat}$ illustrated in FIG. 20A to be determined. The distances $d_{Med}$ and $d_{Lat}$ may be defined as the distances between the hinge point 606 of the pivoting tensioner and the attachment points of the medial and lateral collateral ligaments, perpendicular to tensions $T_{med}$ and $T_{lat}$.

Resolving the forces vertically in FIG. 20A yields:

a. $F_{distraction}=T_{Med}+T_{Lat}$

Here it may be assumed that the sum of moments around the hinge point 606 is zero. Hence:

a. $T_{Med}\times d_{Med}=T_{Lat}\times d_{Lat}$ and thus a. $T_{Med}=F_{distraction}-T_{Lat}$ i. $=F_{distraction}-(T_{Med}\times d_{Med})/d_{Lat}$ ii. $=(F_{distraction}\times d_{Lat})/(d_{Lat}+d_{Med})$ and a. $T_{Lat}=F_{distraction}-T_{Med}$ i. $=F_{distraction}-(T_{Lat}\times d_{Lat})/d_{Med}$ ii. $=(F_{distraction}\times d_{Med})/(d_{Med}+d_{Lat})$.

Figure 20B:
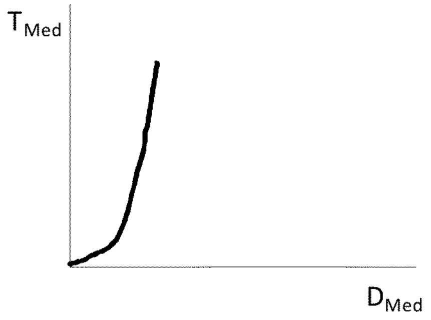
FIGS. 20B and 20C show graphs illustrating an example of the measured force-distance characteristics of a knee joint at a particular knee angle, using the approach shown in FIG. 20A.
Figure 20C:
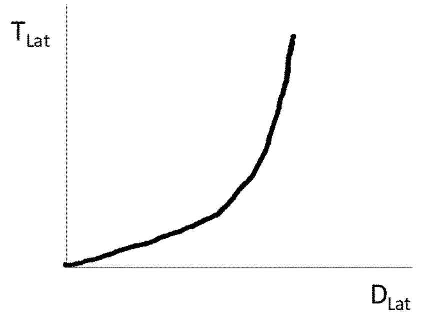

Accordingly, the tension in the medial collateral ligament (see FIG. 20B) and in the lateral collateral ligament (see FIG. 20C) as a function of displacement, at a given knee flexion angle, may be determined without the need for separate medial and lateral force sensors.

In this specification, example embodiments have been presented in terms of a selected set of details. However, a person of ordinary skill in the art would understand that many other example embodiments may be practiced which include a different selected set of these details. It is intended that the following claims cover all possible example embodiments.

Any instructions and/or flowchart steps can be executed in any order, unless a specific order is explicitly stated. Also, those skilled in the art will recognize that while one example set of instructions/method has been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are covered as well.

The invention claimed is:

1. A surgical method, comprising:

inserting a knee tensioner into a patient's knee joint, moving the patient's knee joint through a plurality of knee flexion angles, operating the knee tensioner while moving the patient's knee joint through the plurality of knee flexion angles to distract a femur and a tibia of the patient's knee joint, measuring lateral resulting force data items and medial resulting force data items at a number of knee flexion angles of the plurality of knee flexion angles, measuring medial knee gap data items and lateral knee gap data items at each of the number of knee flexion angles, and operating a data processing apparatus, including:

storing the measured medial knee gap data items and the measured medial resulting force data items and the measured lateral knee gap data items and the measured lateral resulting force data items for each of the number of knee flexion angles;

determining a lateral force-distance characteristic for each of the number of knee flexion angles based on at least the measured lateral resulting force data items and the measured lateral knee gap data items;

determining a medial force-distance characteristic for each of the number of knee flexion angles based on at least the measured medial resulting force data items and the measured medial knee gap data items;

using the lateral force-distance characteristic for each of the number of knee flexion angles to determine a lateral knee gap distance corresponding to a lateral target force for each of the number of knee flexion angles;

using the medial force-distance characteristic for each of the number of knee flexion angles to determine a medial knee gap distance corresponding to a medial target force for each of the number of knee flexion angles;

outputting the lateral knee gap distance corresponding to the lateral target force and the medial knee gap distance corresponding to the medial target force for each of the number of knee flexion angles;

for each of the number of knee flexion angles, using the lateral force-distance characteristic to determine a variation in lateral knee gap distance corresponding to a variation in the lateral target force;

for each of the number of knee flexion angles, using the medial force-displacement characteristic to determine a variation in medial knee gap distance corresponding to a variation in the medial target force; and outputting the variation in lateral knee gap distance with the lateral knee gap distance and the variation in medial knee gap distance with the medial knee gap distance.

2. The surgical method of claim 1, wherein each of the medial and lateral target forces for each of the number of knee flexion angles is a pre-selected value.

3. The surgical method of claim 1, wherein each of the medial and lateral target forces for each of the number of knee flexion angles is determined from the lateral force-distance characteristic and from the medial force-distance characteristic for each of the number of knee flexion angles.

4. The surgical method of claim 3, wherein the lateral target force is based on a cross over force at which the lateral force-distance characteristics change from a first behavior to a second behavior over the number of knee flexion angles, and wherein the medial target force is based on a cross over force at which the medial force-distance characteristics change from a first behavior to a second behavior over the number of knee flexion angles.

5. The surgical method of claim 1, further comprising:

receiving a thickness of a planned tibial component;

determining a planned lateral knee gap and a planned medial knee gap arising from the thickness of the planned tibial component as a function of knee flexion angle over the number of knee flexion angles;

using the lateral force-distance characteristics to determine a predicted lateral force corresponding to the planned lateral knee gap as a function of knee flexion angle over the number of knee flexion angles;

using the medial force-distance characteristics to determine a predicted medial force corresponding to the planned medial knee gap as a function of knee flexion angle over the number of knee flexion angles; and outputting the predicted lateral forces and the predicted medial forces as a function of knee flexion angle over the number of knee flexion angles.

6. The surgical method of claim 5, wherein the predicted lateral forces as a function of knee angle over the number of knee flexion angles and the predicted medial forces as a function of knee flexion angle over the number of knee flexion angles are output together with the output of the lateral knee gap distances corresponding to the target forces and the medial knee gap distances corresponding to the lateral and medial target forces respectively as a function of knee flexion angle over the number of knee flexion angles.

7. The surgical planning method of claim 5, and further comprising receiving a further thickness of the planned tibial implant, and repeating the steps of claim 5 using the further thickness.

8. The surgical method of claim 1, wherein the measured medial knee gap data items and the measured lateral knee gap data items are derived from tracking data received from a tracking system.

9. The surgical method of claim 1, wherein the measured medial resulting force data items and the measured lateral resulting force data items are derived from measurements received from an electronic force sensor.

10. A method comprising:

inputting a planned tibial component thickness;

inserting a knee tensioner into a patient's knee joint;

moving the patient's knee joint through a plurality of knee flexion angles;

operating the knee tensioner while moving the patient's knee joint through the plurality of knee flexion angles to distract a femur and a tibia of the patient's knee joint;

measuring a lateral force-distance characteristic and a medial force-distance characteristic of the patient's knee joint at each of the plurality of knee flexion angles;

determining a lateral knee gap corresponding to a lateral target force as a function of knee flexion angle over the plurality of knee flexion angles from the lateral force-distance characteristics;

determining a medial knee gap corresponding to a medial target force as a function of knee flexion angle over the plurality of knee flexion angles from the medial force-distance characteristics;

using the medial knee gap and the lateral knee gap as a function of knee flexion angle to assess a total knee gap based on the medial knee gap and the lateral knee gap arising from a planned knee replacement procedure to be carried out on the patient's knee joint;

using the lateral force-distance characteristics to determine predicted lateral forces corresponding to the planned tibial component thickness as a function of knee angle over the plurality of knee flexion angles;

using the medial force-distance characteristics to determine predicted medial forces corresponding to the planned tibial component thickness as a function of knee angle over the plurality of knee flexion angles; and displaying the predicted lateral forces and the predicted medial forces as a function of knee angle over the plurality of knee flexion angles.

* * * * *